United States Patent [19]

Elliott et al.

[11] 4,024,163

[45] May 17, 1977

[54] INSECTICIDES

[75] Inventors: Michael Elliott, Harpenden; Norman Frank Janes, Luton; David Allen Pulman, Harpenden, all of England

[73] Assignee: National Research Development Corporation, London, England

[22] Filed: Aug. 13, 1974

[21] Appl. No.: 497,056

Related U.S. Application Data

[63] Continuation-in-part of Ser. No. 363,318, May 24, 1973, abandoned.

[30] Foreign Application Priority Data

| May 25, 1972 | United Kingdom | 24809/72 |
|---|---|---|
| May 25, 1972 | United Kingdom | 24810/72 |
| June 30, 1972 | United Kingdom | 30838/72 |
| Dec. 21, 1972 | United Kingdom | 59184/72 |
| Apr. 30, 1973 | United Kingdom | 20539/73 |

[52] U.S. Cl. .................. 260/347.4; 260/326 A; 260/465 D; 260/468 H; 260/347.4; 260/544 L; 260/501.1; 260/501.17; 260/274; 260/285; 260/304 R; 260/306

[51] Int. Cl.$^2$ ............... C07C 69/74; C07C 121/75; C07C 307/54; C07C 204/18

[58] Field of Search ........ 260/468 H, 465 D, 347.4

[56] References Cited

UNITED STATES PATENTS

| 3,509,180 | 4/1970 | Elliot | 260/347.4 |
|---|---|---|---|
| 3,666,789 | 5/1972 | Itaya et al. | 260/468 |
| 3,683,005 | 8/1972 | Sota | 260/468 |
| 3,761,506 | 9/1973 | Osbond et al. | 260/468 |
| 3,766,218 | 10/1973 | Veda et al. | 260/347.4 |
| 3,813,427 | 5/1974 | Osbond et al. | 260/468 |
| 3,835,176 | 9/1974 | Matsuo et al. | 260/465 |
| 3,847,944 | 11/1974 | Ohno et al. | 260/332.2 |
| 3,850,977 | 11/1974 | Itaya et al. | 260/468 |
| R28,110 | 8/1974 | Osbond et al. | 260/468 |

FOREIGN PATENTS OR APPLICATIONS

A95,346   8/1970   France ........................ 260/468

OTHER PUBLICATIONS

Forkas et al., Chem. Listy. 52 688 (1958).

*Primary Examiner*—Robert Gerstl
*Attorney, Agent, or Firm*—Cushman, Darby & Cushman

[57] ABSTRACT

New insecticides are of formula:

$$R^3(R^2)C=C(R^1)-CH\underset{\underset{CH_3}{\diagdown}\underset{CH_3}{C}\diagup}{\diagdown\diagup}CH-COOR$$

wherein $R^1$ represents hydrogen or a methyl group; $R^2$ represents hydrogen or a halogeno or lower alkyl group; $R^3$ represents hydrogen or a halogeno, lower alkyl (which is different to $R^2$ when $R^2$ represents a lower alkyl group) or carbo(loweralkoxy) group which contains at least 2 carbon atoms in the lower alkoxy residue when $R^2$ represents methyl or $R^2$ and $R^3$ together with the carbon atom to which they are attached represent a cycloalkylene ring having at least one endocyclic carbon to carbon double bond; with the proviso that (a) $R^2$ and $R^3$ each represent hydrogen only when $R^1$ represents methyl and (b) $R^3$ contains at least 2 carbon atoms when $R^1$ and $R^2$ each represent hydrogen; and R represents a group which form insecticidal esters with chrysanthemic acid e.g. 5-benzyl-3-furylmethyl, 3-phenoxybenzyl, α-cyano-3-phenoxybenzyl. The esters are prepared by forming the ester linkage conventionally or by a Wittig reaction using a 3-formyl- or 3-acetyl-2,2-dimethyl cyclopropane carboxylic acid esterified with the desired residue or by an alkyl group which is subsequently converted to the desired residue.

34 Claims, No Drawings

INSECTICIDES

This application is a continuation in part for copending Application Ser. No. 363,318 filed May 24th 1973, now abandoned.

This invention relates to insecticides and more particularly to synthetic insecticides of the pyrethrin type, to their preparation, to compositions containing them and to the insecticidal use of the compounds and compositions.

For many years, research has been pursued in the field of synthetic analogues of the pyrethrins to discover synthetic substitutes having properties superior to those of the natural products. Ideally, synthetic analogues of the naturally occurring pyrethrins should compare well with or be superior to the natural products as regards level of toxicity to insects and mammals, insecticidal spectrum and knock down properties and, in addition, should offer ease of manufacture.

Since the discovery that the naturally occurring pyrethrins were esters of certain substituted cyclopropane carboxylic acids and substituted cyclopentenolones, the search for synthetic analogues concentrated initially on modifying the "alcohol" part of the ester molecule and later on modifying the "acid" part of the ester molecule or, in some cases, modifying both parts of the ester molecule. The naturally occurring esters are esters of chrysanthemic or pyrethric acids of the formula:

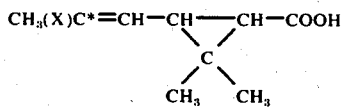

where X represents a methyl group (chrysanthemic acid) or a carbomethoxy group (pyrethric acid).

We have now found that a high level of insecticidal activity and a particularly valuable combination of toxicity and knock-down properties can be obtained in esters of 2,2-dimethyl-3-alkenyl cyclopropane carboxylic acid where the substitution on the 3-alkenyl side chain differs from that of all previously known pyrethrin-like esters, having high insecticidal toxicity and low mamalian toxicity, certain esters of the invention also have exceptionally good photo stability.

Accordingly, the present invention provides esters of the general formula:

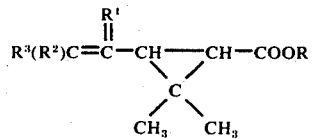

wherein $R^1$ represents hydrogen or a methyl group; $R^2$ represents hydrogen or a halogeno or alkyl group; $R^3$ represents hydrogen or a halogeno, alkyl (which differs from $R^2$ when $R^2$ represents an alkyl group) or carboalkoxy group which contains at least 2 carbon atoms in the alkoxy residue when $R^2$ and $R^3$ together with the carbon atom to which they are attached represent a cycloalkylene ring having at least one endocyclic carbon to carbon double bond; with the proviso that (a) $R^2$ and $R^3$ each represent hydrogen only when $R^1$ represents methyl and (b) $R^3$ contains at least 2 carbon atoms when $R^1$ and $R^2$ each represent hydrogen and (c) when one of $R^2$ and $R^3$ represents halogeno, the other of $R^2$ and $R^3$ represents hydrogen or halogen or carboalkoxy; and R represents (a) hydrogen (or a salt of acid halide derivative of the acid) or an alkyl group, or (b) a group of formula

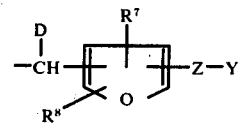

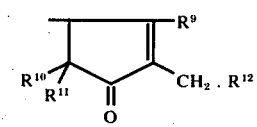

or

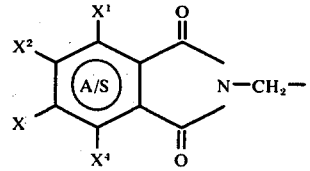

or

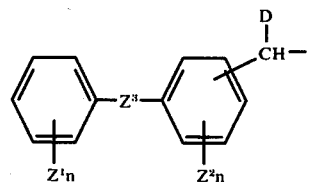

or

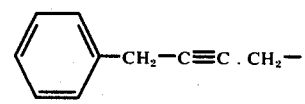

or

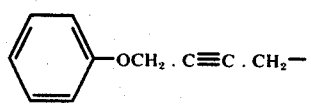

wherein Z represents O, S, $CH_2$ or CO, Y represents hydrogen or an alkyl, alkenyl or alkynyl group or an aryl or furyl group which is unsubstituted or substituted in the ring by one or more alkyl, alkenyl, alkoxy or halogeno groups, $R^7$ and $R^8$, which may be the same or different, each represent hydrogen or an alkyl, or alkenyl group, $R^9$ represents hydrogen or a methyl group, $R^{10}$ and $R^{11}$, which may be the same or different, each represent hydrogen or an alkyl group, $R^{12}$ represents an organic radical having carbon-carbon unsaturation in a position α to the $CH_2$ group to which $R^{12}$ is attached.

A/S indicates an aromatic ring or a dihydro or tetrahydro analogue thereof, $X^1$, $X^2$, $X^3$ and $X^4$, which may be the same or different, each represent hydrogen, chlorine or a methyl group, $Z^3$ represents $-CH_2-$ or $-O-$ or $-S-$ or $-CO-$, D represents H, CN or $-C \equiv CH$, $Z^1$ and $Z^2$, which may be the same or different, each represent chlorine or a methyl group and $n = 0$, 1 or 2, with the proviso that R does not represent hydrogen (or an acid chloride derivative of the acid) or an ethyl or allethronyl group when $R^1$ represents hydrogen, $R^2$ and $R^3$ each represent chlorine and the compound is racemic.

The esters of the present invention where R represents a group of formula III, IV, V, VI, VIA or VIB are insecticidal esters having a valuable combination of toxicity and knock down properties. The level of insecticidal activity of the new compounds is surprisingly high, the crystalline isomer of α-cyano-3-phenoxy benzyl —[1R - cis]-2,2-dimethyl-3-(2,2-dibromovinyl)cyclopropane carboxylate being 23 and 14 times respectively more toxic to houseflies and mustard beetles than 5-benzyl-3-furylmethyl-(+)-trans chrysanthemate while many other esters of the invention have toxicities up to about 10 times that of the chrysanthemate.

The esters of the present invention where R represents alkyl are not insecticidal but are useful intermediates in the production of the insecticidal esters e.g. by transesterification. As will be discussed in more detail below, the new alkyl esters of the present invention can be prepared in that form by a Wittig synthesis and it is not necessary to convert the alkyl ester into the free carboxylic acid in order to produce the insecticidal esters of the invention. However, if desired, the alkyl esters can be converted into the free carboxylic acid, e.g. by hydrolysing the ester to give a salt and subsequently acidifying the salt.

The esters of the present invention where R represents alkyl and $R^2$ = carboalkoxy are useful intermediates in the production of the insecticidal esters which can be converted by acid catalysis, e.g. using toluene-4-sulphonic acid in benzene, to the corresponding free carboxylic acid without affecting the carboalkoxy group $R^2$. As will be discussed in more detail below, the new alkyl esters of the present invention are prepared in that form by a Wittig synthesis and it is necessary to convert the alkyl ester into the free carboxylic acid in order to produce the insecticidal esters of the invention. This is best achieved selectively utilising a t-butyl ester (R = t-butyl). However, if desired, a t-butyl or other alkyl ester can be converted into the free carboxylic acid, by partial saponification but it is difficult to prevent saponification of the carboalkoxy group $R^2$ at the same time.

The insecticidal esters of the present invention may be regarded structurally as esters of a 3-substituted-2,2-dimethylcyclopropane carboxylic acid and an alcohol e.g. a benzyl alcohol, a furylmethyl alcohol, a cyclopenteneolone or an α-cyano, or α-ethynyl benzyl or α-cyano or α-ethynyl-furylmethyl-alcohol. While the esters may be conveniently described structurally in these terms, it will be appreciated and explained in more detail below, that the esters can be prepared by methods other than esterifying the acid with the alcohol and, in practice, often are.

So far as the various values of $R_1$, $R^2$ and $R^3$ are concerned, it is preferred that when these groups represent alkyl, or carbo-alkoxy groups, the groups contain up to 6 carbon atoms, and, more particularly, up to 3 carbon atoms, methyl, ethyl, propyl, carbo-methoxy, carbo-ethoxy, and carbo-propoxy, being of particular interest. When $R^2$ and/or $R^3$ represents a halogeno group, it is preferably fluorine, chlorine or bromine. When $R^2$ and $R^3$ each represent halogeno they are preferably, but not necessarily the same halogen.

The esters of the present invention fall into various sub-classes structurally, depending primarily upon the nature of substituent $R^2$ and $R^3$. One sub-class of particular interest are those compounds where $R^1$ and $R^3$ each represent hydrogen and $R^2$ represents an alkyl group of at least two carbon atoms. We have now found that in this sub-class the highest toxicity to houseflies and mustard beetles of 5-benzyl-3-furylmethyl esters of 3-β-alkylvinyl-2,2-dimethylcyclopropane carboxylic acid is shown when the alkyl group is ethyl.

Further sub-classes of particular interest are those esters where $R^1$ and $R^3$ each are hydrogen and $R^2$ is chlorine or bromine and those compounds where $R^1$ is methyl and $R^2$ is hydrogen, and $R^3$ is hydrogen or an alkyl group containing up to 6 carbon atoms such as methyl, ethyl or propyl.

Many of the above sub-classes of esters are those where the carbon atom in the β position in the 3-substituent is directly bonded to at least one hydrogen atom. A further sub-class of ester of the present invention is one where the substitution at the asterisked carbon atom differs from that of all previous compounds by being an unsymmetrical dialkyl substitution and of this class of compound, whose where one of $R^2$ and $R^3$ is methyl and the other is ethyl are of interest. When $R^2$ and $R^3$ together with the carbon atom to which they are attached form a cyclic group, it is preferred that the ring be one containing 5 carbon atoms and 1 or 2 endocyclic carboncarbon double bonds.

Another sub-class of particular interest are those compounds where $R^3$ represents hydrogen and $R^2$ represents a carboalkoxy group. These esters are esters of a demethyl pyrethric acid analogue which is devoid of the methyl substituent on the β carbon atom of the 3-substituent. A further sub-class of considerable importance are those esters where $R^3$ represents methyl and $R^2$ represents a carboalkoxy group, where the alkoxy residue contains at least two carbon atoms. These esters are esters of the pyrethric acid analogues which do not contain the carbomethoxy substituent on the β carbon atom of the 3-substituent.

Further sub-classes of particular interest are those esters where $R^3$ represents an alkyl group of at least two carbon atoms; again these esters are esters of a pyrethric acid homologue which does not contain the methyl substituent on the asterisked carbon atom of formula I. In these esters, $R^2$ may represent the carbomethoxy group (which is present in pyrethric acid) or a higher homologue thereof.

The most active of the insecticidal esters of the invention are those where $R^1$ represents hydrogen and $R^2$ and $R^3$, each represents a halogeno group, the 5-benzyl-3-furylmethyl esters of the various isomeric 2,2-dimethyl-3-(2,2-dichlorovinyl)-cyclopropane carboxylic acids being up to 2½ times more toxic to houseflies than the corresponding ester of (+)-trans-chrysanthemic acid, itself 50 times more toxic to normal houseflies than natural pyrethrin I. Esters of these acids with 3-phenoxybenzyl- and α-cyano-3-phenoxybenzyl alcohol give esters which are 2 to 11 times more toxic than 5-benzyl-3-furylmethyl (+)-trans chrysanthemate. Esters of these 3-dihalovinyl acids with 3-phenoxybenzyl alcohol and α-cyano-3-phenoxy benzyl alcohol are also of particular value because of their great light stability than the corresponding chrysanthemates.

A further halogenated sub-class of interest are those esters where $R^1$ represents hydrogen, $R^2$ repersents halogeno and $R^3$ represents carboalkoxy. The acid residues in these esters are analogues or pyrethric acid where the methyl substituent on the β-carbon atom of the 3-substituent is replaced by halogeno and homologues of these acids where the carbomethoxy group is replaced by a carboalkoxy group containing at least 3 carbon atoms. The halogen is preferably chlorine or bromine and the carboalkoxy group is preferably carbo-methoxy, -ethoxy or -n-propoxy.

Preferred esters of the present invention include those which are structurally esters of a 2,2-dimethyl-3-substituted cyclopropane carboxylic acid where the 3-substituent is:

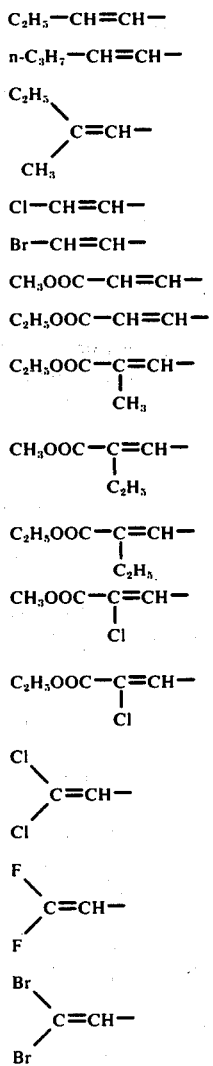

When the esters of the present invention are alkyl esters, it is preferred that the alkyl group be one containing up to 6 carbon atoms and we have found that methyl, ethyl and tertiary butyl esters are amongst those which can be readily prepared by our synthetic methods.

When the ester is one structurally derived from a furylmethyl alcohol it is preferred that the furylmethyl alcohol be one of the 3-furylmethyl alcohols described in British Patent Specification No. 1,168,798. In the furylmethyl alcohols, and particularly in the 3-furylmethyl alcohols, it is preferred that $R^7$ and $R^8$ each represent hydrogen or groups containing up to 4 carbon atoms, particularly a methyl group and that Y represents a phenyl group which is unsubstituted or substituted in the ring by a group containing up to 4 carbon atoms, e.g. methyl or methoxy, or by chlorine, and Z=$CH_2$, and D=H. Analogues of these compounds whre Z=O, S or CO and D=CN or C ≡ CH can also be used. Other compounds of interest are those where Y represents a hydrogen atom, an alkyl group containing up to 4 carbon atoms, an alkenyl group containing up to 4 carbon atoms, e.g. vinyl, an alkadienyl group containing up to 4 carbon atoms or an alkynyl group e.g. propargyl or a furyl group.

Specific alcohols of this category, from which the esters of the invention are structurally derivable, include 5-benzyl-3-furylmethyl alcohol, 5-benzyl-2-methyl-3-furylmethyl alcohol, 5-benzylfurfuryl alcohol, 4-benzyl-5methyl-furfuryl alcohol, 5-p-xylyl-furfuryl alcohol, 2,4,5-trimethyl-3-furylmethyl alcohol, 4,5-dimethylfurfuryl alcohol, 5-phenoxy- and 5-benzoyl-3-furylmethyl alcohol and α-cyano and α-ethynyl-5-benzoyl-and 5-phenoxy-3-furylmethyl alcohol.

The cyclopentenolones from which the esters of the invention are structurally derivable are those unsubstituted in the 3-position or those substituted in the 3-position by a methyl group, ($R^9$ = H or $CH_3$).

The cyclopentenolones unsubstituted in the 3-position are described in British Patent Specification No. 1,305,025. Some of these alcohols are the 3-demethyl analogues of the alcohols from which the naturally occurring pyrethrins are derived. In the present invention, it is preferred that $R^{10}$ and $R^{11}$ each represent hydrogen, methyl or ethyl and $R^{12}$ represents an aryl group such as a phenyl group or a phenyl group substituted by a halogeno or alkyl or alkoxy substituent, of 1 to 4 carbon atoms, for example tolyl, xylyl, p-chlorophenyl or p-methoxyphenyl $R^{12}$ may also represent a 2- or 3-furyl group or an alkenyl group such as a vinyl, prop-1-enyl or buta-1,3-dienyl group.

When the esters of the invention are structurally derivable from the cyclopentenolones which are substituted in the 3-position by the methyl group, ($R^9$ = methyl), the esters may be derived from allethrolone ($R^{10} = R^{11}$ = H, $R^{12}$ = vinyl), pyrethrolone ($R^{10} = R^{11}$ = H, $R^{12}$ = buta-1,3-dienyl), cinerolone ($R^{10} = R^{11}$ = H, jasmolone ($R^{10} = R^{11}$ = H, $R^{12}$ = but-1-enyl) or furethrolone ($R^{10} = R^{11} = R^{12}$ — 2-furyl).

When the esters of the invention are phthalimidomethyl esters where R is of formula V, they may be phthalimido, dihydrophthalimido or tetrahydrophthalimido-methyl esters where the phthalimido, dihydrophthalimido or tetrahydrophthalimido residue is one described in British Patent Specification Nos. 985,006, 1,052,119 or 1,058,309. 3,4,5,6-Tetrahydrophthalimidomethyl esters are of particular interest.

When the esters of the invention are those where R is of formula VI, it is preferred that they be 3-benzylbenzyl esters, 3-benzoylbenzyl esters or 3-phenoxybenzyl esters although each of the rings may be substituted by up to 3 chloro and/or methyl groups. Other esters of particular interest where R is of formula VI are those where $Z^3$ represents O or $CH_2$ and D represents -CN or -C ≡ CH, e.g. esters of α-cyano- or α-ethynyl-3-phenoxybenzyl alcohol and of α-cyano- or α-ethynyl-3-benzyl- and 3-benzoylbenzyl alcohols.

The compounds of the present invention exhibit geometrical and optical isomerism and consequently may be prepared in optically active forms which may subsequently be mixed together or as racemic mixtures which may subsequently be resolved into optically active forms. In addition, optically active forms or racemic mixtures can be separated into the individual geometrical isomers. In addition to the geometrical isomerism that results from the configuration of the substituents on the cyclopropane ring with respect to one another and the ring, there is also the possibility of geometrical isomerism in the side chain on position 3 when $R^1$, $R^2$ and $R^3$ are such that the unsaturated side-chain is unsymmetrically substituted. In the α-cyano- and α-ethynyl compounds (D=CN or C≡CH), there is further possibility of optical isomerism and the compounds envisaged include esters of both the racemic mixture and of the separate isomers resulting from the assymetry at the carbon atom bearing the D group. The various optical and geometrical isomers of the esters of the invention usually have different insecticidal toxicities and knock down potency.

The compounds of the invention having the hydrogen atoms on the 1 and 3 positions of the cyclopropane ring in the trans-relationship to one another are stereo analogues of (+)-trans-chrysanthemic acid and for this reason represent a preferred class of compounds of the invention but the present invention also includes compounds where the two hydrogen atoms in question are in the cis-relationship. Thus highly active esters are derived from (+)-trans and (+)-cis- acids but (±)-trans, and (±)-cis, are also of interest, as well as mixtures of (+)-trans and (+)-cis and (±)-trans and (±)-cis with varying relative proportions of the cis and trans isomers.

When $R^1$ represents hydrogen and $R^2$ and $R^3$ each represent chlorine, then particularly potent compounds are unexpectedly obtained when the configuration about the cyclopropane ring is cis and R represents 5-benzyl-3-furylmethyl- or 3-phenoxybenzyl or α-cyano analogues of these two groups. When $R^1$ represents hydrogen and $R^2$ and $R^3$ each represent fluorine or bromine and R represents 5-benzyl-3-furylmethyl, potent toxic and/or knock down agents are obtained when the cyclopropane ring is in either the cis or trans configurations but the cis isomers tend to be the more potent in the dibromo series also. Particularly potent compounds of this type are obtained when the ester is in the form of a substantially pure optical isomer with respect to the cyclopropane ring and the ester has [R] configurations at C, of the cyclopropane ring. We refer above to (±)-cis, (±)-trans, (+)-trans etc., in relation to stereochemistry. We have used this nomenclature to refer to compounds where the stereochemistry about the cyclopropane ring is equivalent to (±)-cis, (±)-trans, (+)-trans etc., chrysanthemic acid. For compounds of the invention which are substantially pure optical and geometrical isomers, we are using the nomenclature [1R,cis] and [1R,trans] as a convenient alternative to the strict nomenclature based on the sequence rule (Cahn. RS., Ingold C and Prelog V, Angew. Chem. Int. Ed. 5 385 (1966)) where, for example, dihalovinyl cyclopropane carboxylates formally derived from (+)-trans-[1R,3R]-chrysanthemates by replacement of the vinyl methyl groups would be [1R,3S]. In accordance with our proposal, compounds we previously designated (+)-cis-[1R,3S] and (+)-trans[1R,3R]- are now designated [1R,cis] and [1R,trans] respectively.

The insecticidal esters of the present invention may be prepared by esterification involving the reaction of an alcohol or derivative thereof of formula R-Q e.g. of formula VII, VIII or VIIIA, and a cyclopropane carboxylic acid or derivative thereof of formula IX,

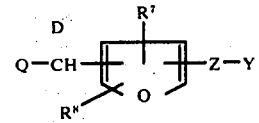
VII

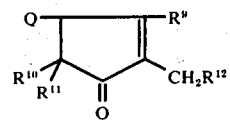
VIII

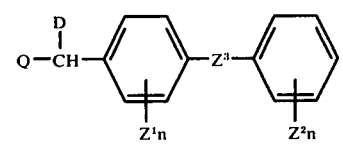
VIIIA

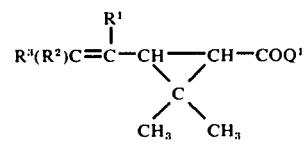
IX where Q and $COQ^1$ are functional groups or atoms which will react together to form an ester linkage and R, $R^1$, $R^2$, $R^3$, $R^7$, $R^8$, $R^9$, $R^{10}$, $R^{11}$, $R^{12}$ and D, Z, $Z^1$, $Z^2$, $Z^3$, Y and n are as defined above.

It is usually convenient in practice either to react the acid or acid halide with the alcohol ($COQ^1$=COOH or Co- halide and Q = OH) or to react a halogeno compound (Q = halogen) with a salt of the carboxylic acid ($COQ^1$=$COO^-M^+$ where M is, for example, a silver or triethylammonium cation).

For reasons which will shortly be described, reactant IX normally becomes available initially in the form of a lower alkyl ester, ($COQ^1$ = COO alkyl) where the alkyl group contains 1 to 6 carbon atoms and consequently, a particularly convenient way of preparing the insecticidal esters of the invention, except where $R^2$ is carboalkoxy, is to subject the alkyl ester of formula IX to transesterification using an alcohol ROH, e.g in the presence of a basic catalyst. When the alkyl ester contains a base sensitive group, e.g. $R^2$ = carboalkoxy, base catalysed transesterification is undesirable and can be avoided by preparing a t.-butyl ester which can be converted into the free acid by acid catalysed decomposition and the free carboxylic group esterified directly or via a salt or halide.

The esters of the present invention can also be prepared by reaction between a phosphorane or ylide of formula X and an ester of 2,2-dimethyl cyclopropane carboxylic acid substituted at the 3-position by an acetyl group or an aldehyde group of formula XI:

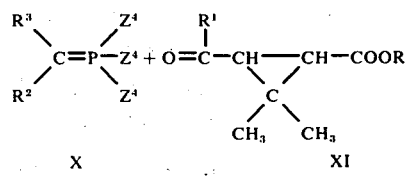

In formulae X and XI $R^1$, $R^2$, $R^3$ are as defined above and R is a group as defined above which will not interfere in the Wittig reaction and $Z^4$, which in principle can represent any organic radical, will normally be a phenyl radical since the stability of the trisubstituted phosphorus oxide which is formed as the by-product in the reaction is particularly high and this favours completion of the reaction between the phosphorane X and the aldehyde or ketone XI.

Esters of the present invention where $R^1$ represents hydrogen can be prepared by reaction with an aldehyde of formula XI while esters of the invention where $R^1$ represents methyl can be prepared by reaction of a 3-acetyl compound of formula XI. The phosphorane X and aldehyde or ketone XI are preferably reacted in substantially equimolar proportions, conveniently in the solvent in which the phosphorane itself has been prepared. As will be discussed in more detail below, this may be an aromatic hydrocarbon such as benzene or a polar solvent such as dimethyl sulphoxide or a chlorinated hydrocarbon such as dichloromethane. The product can be improved if reaction is carried out in an inert atmosphere e.g. under nitrogen. The reaction between the phosphorane and aldehyde or ketone is normally quite rapid and the desired ester can be recovered from the reaction mixture after a reaction time of less than 1 hour although reaction times of up to 24 hours have been used. The desired ester can be recovered from the reaction product by solvent extraction e.g. with diethyl ether or petroleum ether.

The phosphorane of formula X where neither $R^2$ nor $R^3$ represent halogen can be prepared from the corresponding phosphonium salt which in turn can be prepared by reacting the appropriately substituted methyl halide with a triorganophosphine in accordance with the following reaction scheme:

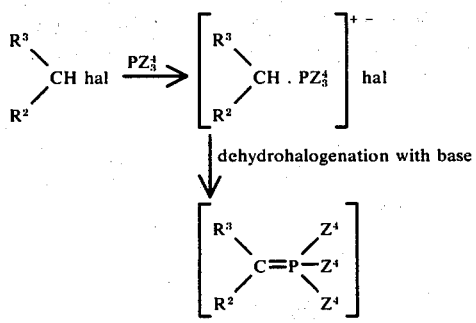

The flexibility of the present synthetic method results from the fact that the initial starting material is the substituted methyl halide $R^3(R^2)CH$ hal and the availability of whole series of such substituted halides permits the production of whole series of 2,2-dimethyl cyclopropane carboxylic acids which are substituted in the 3-position impossible various groups which have previously been difficult or imposible to prepare. In the above-mentioned synthesis of the phosphorane, it is convenient to start with a substituted methyl bromide which is reacted with triphenylphosphine to give the corresponding triphenylphosphonium bromide and subsequently converting the phosphonium salt to the phosphorane or ylide which can be designated by the formula given above. The conversion of the phosphonium salt to the phosphorane can be brought about by treating the phosphonium salt with an alkali metal amide or alkali metal methyl sulphinyl methide ($^-CH_2.SO.CH_3M^+$). For example, sodamide can be prepared by reacting sodium in liquid ammonia and the reaction carried out in the presence of the excess ammonia as the liquid medium. At the end of the reaction, the liquid ammonia can be allowed to evaporate and the phosphorane taken up into an organic solvent such as benzene and the subsequent reaction with aldehyde or ketone XI carried out in this organic solvent. Alternatively, dimethyl sulphoxide can be reacted with sodium hydride to give sodium methyl sulphinyl methide and the production of the phosphonium salt carried out using this reagent and, following formation of the phosphorane, the subsequent reaction with the aldehyde or ketone XI can be carried out in the same reaction medium.

When $R^2$ = carboalkoxy, the conversion of the phosphonium salt to the phosphorane can be brought about by treating the phosphonium salt with an alkali metal amide in liquid ammonia or in aqueous alkali metal hydroxide solution, e.g. 5% NaOH. The liberated phosphorane can be filtered from the solution and subsequently reacted with the aldehyde XI in a suitable solvent e.g. $CH_2Cl_2$.

Phosphoranes where $R^3$ represents carboalkoxy and $R^2$ represents hydrogen or methyl can be prepared by the above described procedures using a haloacetate or α-halopropionate alkyl ester as the substituted methyl halide but this synthesis is not entirely satisfactory for the preparation of phosphoranes of this type where $R^2$ represents an alkyl group of 2 or more carbon atoms. For such higher homologues, a phosphorane where $R^3$ represents hydrogen and $R^2$ represents the desired alkyl group is first prepared as an intermediate by the procedures described above starting from an alkyl halide of at least 3 carbon atoms and this intermediate phosphorane is then reacted with the appropriate alkyl chloroformate ester to introduce the desired carboalkoxy group.

Phosphoranes where $R^2$ and/or $R^3$ represent halogen can be prepared by simple modifications of the above described synthesis.

When $R^2$ and $R^3$ each represent halogen, a carbon tetrahalide can be used in place of the substituted methyl halide and the reaction proceeds in accordance with the equation:

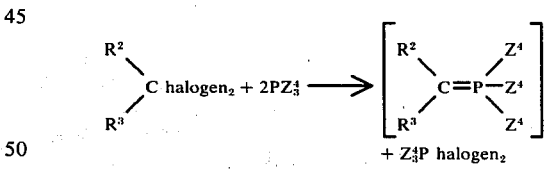

the dehydrohalogenation of the quaternary phosphonium halide proceeding spontaneously.

Halogenated phosphoranes can also be prepared by halogenating an unhalogenated phosphorane, itself obtained by the above described procedures in accordance with the following reaction scheme:

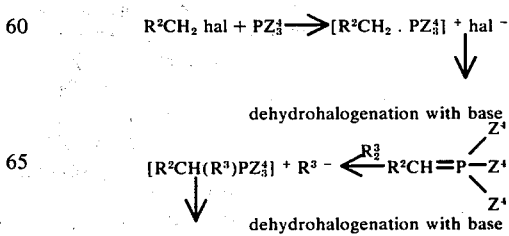

-continued

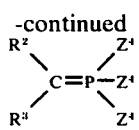

where hal = halogen, $R^3$ = halogen and $R^2$ is as defined above.

We have found that it is desirable that the carboxyl group in the aldehyde or ketone reactant XI be esterified as a lower alkyl ester in order to achieve the most satisfactory results in the reaction with the phosphorane X. This means that the alkyl esters of the present invention are produced directly and, since it is possible to convert these alkyl esters into the insecticidal esters of the invention, except those containing a base sensitive group, e.g. $R^2$ = carboalkoxy, by a simple base catalysed transesterification reaction, it is not necessary to convert the alkyl esters of the invention into the corresponding acid in order to produce the insecticidal esters. However, indirect conversion of the alkyl esters to the insecticidal esters is possible in accordance with the present invention and, when operating in accordance with this embodiment, the carboalkoxy group in the ester of formula II can be converted by conventional hydrolysis into the corresponding free carboxylic acid group going, via the alkali metal or other salt for instance, and this carboxylic acid can be directly esterified as described above or alternatively can be converted first into an acid halide e.g. the chloride and this acid halide converted into an ester by reaction with an appropriate alcohol of formula ROH as described above.

In the case where R is a t.-butyl group, the alkyl ester can be converted into the free acid by heating with a small amount of toluene-4-sulphonic acid. This reaction can be carried out in benzene and the resulting carboxylic acid converted to the acid chloride in the benzene solution without isolation.

In the synthetic methods described so far, alkyl esters of the invention are prepared by a Wittig reaction between a phosphorane X and an alkyl ester of a carbonyl compound XI and the resulting alkyl ester of the invention converted to an insecticidal ester by transesterification or via the free acid and acid chloride which is subsequently reesterified e.g. with 5-benzyl-3-furylmethyl alcohol. It is usually most convenient to operate in this manner but is not essential to do so and a practical alternative is to produce the insecticidal ester directly by reacting the phosphorane X with a carbonyl compound of formula XI where R represents a group of formula III, IV, V, VI, VIA or VIB or VIB as defined above.

Such carbonyl compounds of formula XI may be prepared by the synthetic methods described above but converting the group R from an alkyl group to a group of formula III, IV, V, VI, VIA or VIB before the Wittig reaction instead of after the Wittig reaction as described above.

Carbonyl compounds of formula IX can be prepared by ozonolysis of the corresponding ester of chrysanthemic acid, when oxygenation of the double bond in the isobutenyl side chain occurs. Thus, provided does not contain a group degradable under ozonolysis conditions, the required carbonyl compound XI for this alternative method can be obtained directly by ozonolysis of the chrysanthemate and the ozonlysed chrysanthemate XI used in the Wittig reaction to give the insecticidal ester. Some furan containing compounds are degraded under ozonolysis conditions so the 5-benzyl-3-furylmethyl ester of caronaldehyde cannot be obtained by direct ozonolysis of the corresponding chrysanthemate (it must be obtained in two stages via an alkyl ester of caronaldehyde) but a 3-phenoxybenzyl ester can be so treated.

Acids of the general formula IX $(COO_1,) = COOH)$ where $R^1 = R^2 =$ H and $R^3 =$ an alkyl group containing at least two carbon atoms can be prepared by reaction between 2-ethynyl-3,3-dimethyl cyclopropane carboxylic acid and an appropriate alkyl halide in the presence of an alkali metal followed by catalytic semihydrogenation. Acids where $R^2=R^3 =$ Cl can be prepared by reacting ethyl diazoacetate with 1,1-dichloro-4-methyl-penta-1,3-diene and converting the ethyl ester to the acid.

Alcohols and halides of formula VIII are described in British Patent Specification No. 1,305,025.

Alcohols of formula VII or VIIIA where D represents CN or C CH can be prepared by conventional methods from the corresponding aldehydes. Thus, a furaldehyde or benzaldehyde can be reacted with (a) HCN, conveniently generated in situ from KCN and acid, when addition of HCN occurs forming the cyanhydrin or (b) an alkali metal acetylide in liquid ammonia.

Alcohols of formula ROH where R is a group of formula VI where D represents hydrogen may be prepared by reduction of the corresponding acids or esters e.g. with a hydride, or by conversion of the corresponding halide to an ester e.g. by reaction with sodium acetate, followed by hydrolysis of the ester, or by reaction of formaldehyde with A Grignard reagent derived from the corresponding halide. The halides of formula R-halogen where R is a group of formula VI where D represents hydrogen can be prepared by halomethylation of the compound:

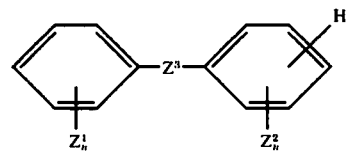

or side chain halogenation of:

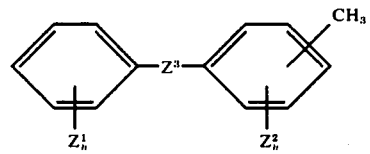

One or more of the insecticidal esters of the invention may be formulated with an inert carrier or diluent to give insecticidal compositions and these may be prepared, for example, in the form of dusts and granular solids, wettable powders, mosquito coils and other solid preparations or as emulsions, emulsifiable concentrates, sprays and aerosols and other liquid preparations after the addition of the appropriate solvents, diluents and surface active agents.

Pyrethrum synergists such as piperonyl butoxide, Sesamex or tropital, may be added to these compositions. Certain insecticidal esters of the invention show significant superiority over structurally similar esters e.g. chrysanthemates or pyrethrates, in the ability to respond to synergists and many esters of the invention have a synergistic factor several times greater than those exhibited by other synthetic esters. Many of the esters derived from acids of the present invention are much more stable to light than those of previously known acids, and dihalovinyl esters are especially favoured in this connection.

The insecticidal compositions may also include known synthetic pyrethrins to improve kill and/or knock down or to synergise the activity of the known pyrethrin and/or that of the synthetic pyrethrins of the invention.

The new esters of the invention or insecticidal compositions containing them may be used for killing insects or controlling the level of insects on a domestic or agricultural scale by treating the insects themselves or an environment susceptible to insect attack with the compounds or compositions.

The following Examples are given to illustrate the present invention (temperatures are in °C., refractive indices are measured at 20° C. Unless otherwise indicated, the hydrogen atoms at $C_1$ and $C_3$ of the cyclopropane ring are in the trans-relationship to one another).

EXAMPLE 1 n-Pentyl triphenylphosphonium iodide (9.5 g., 0.02M), prepared by reaction of n-pentyl iodide with triphenylphosphine, was added slowly, under nitrogen, to soadamide [0.7 g. sodium (0.03M) in liquid ammonia (130 ml.)]. The mixture was stirred for 0.5 hours and the ammonia allowed to evaporate (2 hours). Benzene (130 ml.) was added and the mixture refluxed, under nitrogen, for 0.5 hours, allowed to cool and the supernatant liquid containing the phosphorane decanted off under nitrogen.

The phosphorane solution was added dropwise, under nitrogen, to a stirred solution of methyl transcarbonaldehyde (1.0 g., 0.0064M) (form ozonolysis of methyl ester of (+)-trans-chrysanthemic acid) in dry benzene (15 ml.). The addition was completed in 10 minutes and the solution was stirred or a further 0.5 hours. The solution was evaporated, the residue dissolved in diethyl ether, the organic solution washed with water and dried. Evaporation yielded a colourless mixture which was further extracted with petroleum ether (60°–80°), evaporation of which yielded a colourless liquid b.p. 107°–109°/5 mm., yield (1.07 g., (80%), $n_D$ 1,4622) which was identified by NMR spectroscopy as 2,2-dimethyl-3-(hex-1-enyl)-cyclopropane carboxylic acid methyl ester. (Compound $C^1$).

EXAMPLE 2

The procedure described in Example 1 was repeated replacing the n-pentyl iodide with equivalent amounts of n-propyl iodide or n-butyl bromide, to give alkyl esters of the invention of formula II and of refractive index as indicated below:

| Compound | $R^3$ | $R^2$ | $R^1$ | R | $n_D$ |
|---|---|---|---|---|---|
| A' | $C_2H_5$ | H | H | $CH_3$ | 1.4581 |
| B' | n-$C_3H_7$ | H | H | $CH_3$ | 1.4572 |

In Compound A', the 3-but-1-enyl substituent is in the trans relationship to the cyclopropane ring. Its (+)-cis-[1R,3S]-isomer (in free acid form) was made by the following procedure. (In both Compound A' and its cis isomer, the configuration around the ethylenic double bond in the 3-substituent is cis.)

n-Propylidene phosphorane [prepared by reacting the corresponding phosphonium iodide (7 g.) with sodamide, (sodium (0.7 g.)/liquid ammonia (150 ml.))] in dry benzene (100 ml.) was added dropwise, with stirring, to a solution of the internal hemi-acylal of cis-3-formyl-2,2-dimethyl-cyclopropane carboxylic acid (0.7 g.) (French Patent Specification No. 1,580,475) in benzene (10 ml.), under nitrogen. The benzene was evaporated off and the residue dissolved in methylene chloride (75 ml.) and washed with water and sodium carbonate solution. Acidification of the carbonate extract yielded an acid which was extracted with methylene chloride, dried ($Na_2SO_4$), and evaporated to give (+)-cis- 1R,3S]-3-but-1-ene-2,2-dimethyl-cyclopropane carboxylic acid (0.7 ). (Compound A' cis).

EXAMPLE 3

The procedure described in Example 1 was repeated replacing the methyl trans-caronaldehyde by an equivalent weight of ethyl (+)-cis-trans-3-acetyl-2,2-dimethylcyclopropane carboxylate and replacing the n-pentyl iodide by methyl iodide, ethyl iodide, n-propyl iodide, or n-butyl bromide to give the alkyl esters of formula II as indicated below having the following refractive index:

| Compound | $R^3$ | $R^2$ | $R^1$ | R | $n_D$ |
|---|---|---|---|---|---|
| F' | H | H | $CH_3$ | $C_2H_5$ | 1.4469 |
| G' | (1)$CH_3$ | H | $CH_3$ | $C_2H_5$ | 1.4570 |
| H' | (2)$C_2H_5$ | H | $CH_3$ | $C_2H_5$ | 1.4570 |
| I' | n-$C_3H_7$ | H | $CH_3$ | $C_2H_5$ | 1.4573 |

(1) (2)the stereochemistry of these esters about the double bond αβ to the cyclopropane ring is (1)40:60 and (2)80:20 Z:E.

EXAMPLE 4

A suspension of sodium hydride in oil (0.50 g., approx. 0.0095M NaH) was washed with dry diethyl ether (20ml.) under nitrogen. Dry dimethylsulphoxide (DMSO) (3.5 ml.) was added and the mixture heated to 80° for 0.5 hours. After cooling, a slurry of n-butyl triphenylphosphonium bromide (3.80 g., 0.0104M) (prepared by reaction of n-butyl bromide with triphenylphospine) in DMSO (9 ml.) was added with stirring, the remainder of the slurry being washed in with diethyl ether (10 ml.). The mixture was stirred for 0.5 hours and ethyl 3-acetyl-2,2-dimethyl-cyclopropane carboxylate (1.0 g, 0.0054m) was added. The mixture was thoroughly shaken and stirred for 24 hours under nitrogen. Ice was added and the mixture acidified with aqueous potassium hydrogen sulphate. After diethyl ether extraction, the organic solution was washed with water, saturated sodium chloride solution, and evaporation of the dried solution ($Na_2SO_4$) yielded a solid which on extraction with petroleum spirit (60°–80°) and evaporation yielded a colourless liquid b.p. 112–188°/20 mm., 0.52 g., (43%) $n_D$ 1.4573. This liquid was identified by NMR spectroscopy as the compound of formula II where $R^3$ = n-$C_3H_7$, $R^2$=H, $R^1$=$CH_3$ and R=$C_2H_5$. (Compound I').

EXAMPLE 5

The procedure described in Example 4 was repeated but replacing the n-butyl bromide by an equivalent weight of 2-bromobutane and replacing the ethyl 3-acetyl-2,2-dimethylcyclopropane carboxylate by an equivalent weight of methyl trans-carbonaldehyde to give the compound of formula II where $R^3=C_2H_5$, $R^2=CH_3$, $R^1=H$ and $R=CH_3$ having $n_D$ 1.4643. (Compound E').

EXAMPLE 6

Chloromethylenetriphenylphosphonium chloride (2.1 g., 0.006M) and dry piperidine (0.51 g., 0.006M), in dry diethyl ether (15 ml.) was treated, under nitrogen, with 8% n-butyl lithium in hexane (4.8 ml., [0.388 g., 0.006M]). The mixture was stirred at room temperature for 1.5 hours and t.-butyl trans-caronaldehyde (1.27 g., 0.0064M) in dry benzene (5 ml.) was added. The mixture was left to stir for 3 days and the solution filtered and the residue washed with dry diethyl ether. The filtrate was washed with 10% $H_2SO_4$, water and evaporation of the dried ($Na_2SO_4$) solvent followed by distillation yielded a colourless liquid b.p. 100°/20 mm. (70%). This was identified by NMR spectroscopy as the ester of formula II where $R^3 = Cl$, $R^2 = H$, $R^1 = H$ and $R = t.-C_4H_9$ and was found to have $n_D$ 1.4670. The stereochemistry about the double bond $\alpha\beta$ to the ring was 20:80 Z:E.

The alkyl esters whose preparation is described above in Examples 1 to 6 were then converted into the corresponding 5-benzyl-3-furylmethyl ester by the procedures described below in Examples 7–9.

EXAMPLE 7

0.2 mols of sodium were slowly added to a solution of 2 mols of 5-benzyl-3-furylmethyl alcohol in toluene. When the reaction between the sodium and the alcohol to give the sodium alcoholate was complete, a solution containing about 1 molar proportion of the alkyl ester of formula II in toluene was added and the mixture heated under reflux with separation of the methanol or ethanol evolved in the trans-esterification reaction. After the solution had cooled, the desired 5-benzyl-3-furylmethyl ester was recovered in yields of 50–70%, based on the weight of alkyl ester, by chromatography on alumina. The structure of the esters as being in accordance with formula II was confirmed by NMR spectroscopy and gas/liquid chromatography.

The following insecticidal esters were prepared:

| Compound | $R^3$ | $R^2$ | $R^1$ | $n_D$ | |
|---|---|---|---|---|---|
| A | $C_2H_5$ | H | H | 1.5174 | (trans isomer) |
| A cis | $C_2H_5$ | H | H | 1.5347 | ((+)-cis-[1R,3S] isomer) |
| B | $n-C_3H_7$ | H | H | 1.5177 | |
| C | $n-C_4H_9$ | H | H | 1.5128 | |
| E | $C_2H_5$ | $CH_3$ | H | 1.5090 | |
| F | H | H | $CH_3$* | 1.5157 | |
| G | $CH_3$ | H | $CH_3$* | 1.5206 | |
| H | $C_2H_5$ | H | $CH_3$* | 1.5180 | |
| I | $n-C_3H_7$ | H | $CH_3$* | 1.5118 | |

*These compounds are a mixture of (±)-cis-trans-isomers.

Compounds A–I are all compounds of formula II where R = 5-benzyl-3-furylmethyl.

Compound A cis was prepared from A' cis by treating with thionyl chloride in benzene to convert A' cis to the acid chloride and then reacting the acid chloride with 5-benzyl-3-furylmethyl alcohol in benzene in the presence of pyridine.

EXAMPLE 8

Methyl 2,2-dimethyl-3-(but-1-enyl)-cyclopropane carboxylate (prepared as described in Example 2), (2.8 g.) was refluxed for 1 hour with 1.8 g. NaOH in 70 mls. methanol. The reaction mixture was then diluted with water, acidified and extracted with diethyl ether to give 2.01 g. 2,2-dimethyl-3-(but-1-enyl)-cyclopropane carboxylic acid, $n_D$ 1.4719. The acid was then converted into its acid chloride by reaction with thionyl chloride and the acid chloride then esterified by reaction in benzene with an equimolar amount of (±)-allethrolone, (±) pyrethrolone, 3-benzylbenzyl alcohol or 3-phenoxybenzyl alcohol in the presence of an equimolar amount of pyridine. The reaction mixture was then chromatographed on neutral alumina and the solvent evaporated to give the desired ester. The following insecticidal esters were prepared:

| Compound | $R^3$ | $R^2$ | $R^1$ | R | $n_D$ |
|---|---|---|---|---|---|
| Q | $C_2H_5$ | H | H | (±)-allethronyl | 1.5009 |
| R | $C_2H_5$ | H | H | (+)-pyrethronyl | 1.5159 |
| S | $C_2H_5$ | H | H | 3-benzylbenzyl | 1.5488 |
| T | $C_2H_5$ | H | H | 3-phenoxybenzyl | 1.5439 |

EXAMPLE 9

A mixture of the tertiary butyl ester described in Example 6 (410 mg.) toluene-4-sulphonic acid (47.5 mg.) and dry benzene (15 ml.) were refluxed 2 hours and cooled to give a solution of the corresponding carboxylic acid. Pyridine (163 mg.) and thionyl chloride (213 mg.) were then added, and the mixture allowed to stand for 2 hours to give the acid chloride. A mixture of substantially equimolar proportions of the acid chloride, 5-benzyl-3-furylmethyl alcohol and pyridine was prepared in dry benzene and the mixture cooled and allowed to stand at room temperature overnight. The mixture was then poured through a column of neutral alumina and eluted with benzene to give a compound of formula II where $R^3 = Cl$, $R^2 = H$, $R^1 = H$ and R = 5-benzyl-3-furylmethyl. This ester, designated ester K, has $n_D$ 1.5418.

EXAMPLE 10

Triphenyl phosphine (13 g.) was dissolved in dry benzene (60 ml.) and ethyl bromoacetate (8.3 g.) was added dropwise. The solution was heated at 70° for 2 days, and then cooled and filtered. The residue was washed with benzene and dried to give about 16 g. of (ethoxycarbonylmethyl) triphenylphosphonium bromide. The phosphonium salt (10 g.) was dissolved in water (250 ml.) and 5% aqueous sodium hydroxide was added dropwise with stirring until the solution became alkaline to litmus. The resulting precipitate was filtered off, washed with water and dried. Crystallisation from ethyl acetate/petroleum spirit gave (ethoxycarbonyl methylene) triphenyl phosphorane as a colourless solid in about 80% yield.

The phosphorane (3.2 g., 0.0092M) in dry dichloromethane (30 ml.) was added to t-butyl transcarbonaldehyde (1.5 g., 0.0076M) (from ozonolysis of t.-butyl (±)-trans-chrysanthemic acid) in dichloromethane (30 ml.) with stirring under nitrogen; stirring was continued at room temperature for 2.5 days. The solution was evaporated, and the residue extracted with petroleum spirit (60-80°) which on evaporation and distillation yielded a colourless liquid b.p. 112°/0.7 mm., 1.60 g. (79%) $n_D$ 1.4666 which was identified by NMR spectroscopy and gas/liquid chromatography as a compound of formula II where $R^2$ = carboethoxy, $R^3$ = H and R = t.-butyl. (Compound P19/B').

EXAMPLE 11

The procedure described in Example 10 was repeated but replacing the bromoacetic acid ethyl ester by an equivalent weight of bromoacetic acid methyl ester and by bromoacetic acid propyl ether and making any necessary variations in reaction time or temperature during phosphorane formation, to give compounds of formula II where $R^3$ = H, R = t.-butyl and $R^2$ = carbomethoxy or carbo-n-propoxy, $n_D$ 1.4677 and 1.4723, (compounds P19/A' and P19/C') respectively.

EXAMPLE 12

The procedure described in Example 10 was repeated replacing the bromoacetic acid ethyl ester by an equivalent weight of α-bromopropionic acid ethyl ester and propyl ester. Esters of formula II were obtained where $R^3$ = methyl, R = t.-butyl and $R^2$ = carboethoxy and carbo-n-propoxy, $n_D$ 1.4658 and 1.4712 (Compounds P19/D' and P19/E') respectively.

EXAMPLE 13 n-Propyl triphenyl phosphonium iodide was prepared by the procedure described in Example 10 replacing the ethyl bromoacetate by n-propyl iodide. The phosphonium iodide (9.5 g.) was then treated under nitrogen with the $NaNH_2$, obtained from 0.5 g. Na in 100 mls. liquid $NH_3$ and the $NH_3$ allowed to evaporate over 2 hours. Benzene (120 mls.) was then added, the mixture refluxed for 15 minutes and 1.08 g. methyl chloroformate in 50 mls dry benzene then added dropwise. The mixture was refluxed a further 10 minutes and then cooled, filtered and the benzene removed to leave a phosphorane of formula:

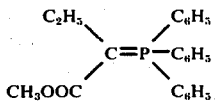

as residue.

The phosphorane was then reacted with t.-butyl caronaldehyde in dichloromethane as described in Example 10 to give a compound b.p. 130°/3 mm., $n_D$ 1.4714 identified as in Example 10 as being of formula II where $R^2$ = $COOCH_3$, $R^2$ = $C_2H_5$, $R^1$ = H and R = t.-butyl. Compound P19/F¹).

The above procedure was also repeated replacing the methyl chloroformate by ethyl and n-propyl chloroformate respectively when the following compounds of formula II were obtained.

| | $R^3$ | $R^2$ | $R^1$ | R | b.p. | $n_D$ |
|---|---|---|---|---|---|---|
| P19/C¹ | $COOC_2H_5$ | $C_2H_5$ | H | t. butyl | 114–116°/1mm. | 1.4682 |
| P19/H¹ | $COOn-C_3H_7$ | $C_2H_5$ | H | t.-butyl | 120°/1mm. | 1.4683 |

EXAMPLE 14

The compound of formula II where $R^2$ = n-propoxy carbonyl, $R^3$ = $CH_3$ and R = t.-butyl (0.393 g.) described in Example 12 was refluxed 2 hours with toluene 4-sulphonic acid (47.2 mg.) in benzene (11.5 ml.).

The solution was cooled and the resulting acid ($R^2$ = n-propoxycarbonyl, $R^3$ = $CH_3$, R = H) crystallised out. Dry pyridine (0.127 g., 131 μl.) and thionyl chloride (0.158 g. 96 μl) were added and the mixture left to stand for 2 hours at about 20° when the corresponding acid chloride formed.

A solution of 5-benzyl-3-furylmethyl alcohol (275 mg.) and pyridine (0.0105 g., 108 μl.) in benzene (8 ml.) was added and the solution left to stand overnight. The resulting solution was passed through a column of neutral alumina and then evaporated to give 550 mg. of a compound of formula II where $R^2$ = n-propoxycarbonyl, $R^3$ = $CH_3$ and R = 5-benzyl-3-furylmethyl, $n_D$ 1.5125. (Compound P19/E). The structure of the ester as being in accordance with formula II was confirmed by NMR spectroscopy and gas/liquid chromatography.

The following esters were prepared by similar methods.

| Compound | $R^3$ | $R^2$ | $n_D$ |
|---|---|---|---|
| P19/A | H | $COOCH_3$ | 1.5262 |
| P19/D | H | $COOC_2H_5$ | 1.5298 |
| P19/C | H | $COOn-C_3H_7$ | 1.5278 |
| P19/D | $CH_3$ | $COOC_2H_5$ | 1.5235 |
| P19/E | $CH_3$ | $COOn-C_3H_7$ | 1.5125 |
| P19/F | $C_2H_5$ | $COOCH_3$ | 1.5228 |
| P19/G | $C_2H_5$ | $COOC_2H_5$ | 1.5193 |
| P19/H | $C_2H_5$ | $COOn-C_3H_7$ | 1.5190 |

Compounds P19/A to P19/H are all compounds of formula II where R = 5-benzyl-3-furylmethyl.

EXAMPLE 15 t.-Butyl-trans-caronaldehyde (1.0 g.) (obtained by ozonolysis of the t.-butyl ester of (+)-transchrysanthemic acid) and triphenyl phosphine (2.65 g.) dissolved in dry carbon tetrachloride (10 ml.) were heated, under nitrogen with stirring, at 60° for 7 hours. The reaction mixture was evaporated under reduced pressure and the residue extracted with diethyl ether ≈ 30 ml.). The organic extract was washed with water, dried (over $Na_2SO_4$) and evaporated. The residue was extracted with petroleum ether (4°–60°) and the solution evaporated and distilled yielding crude product (0.77 g.) (b.p. 100°/1 mm.), which was purified by crystallisation to give t-butyl-(±)-trans[1R,3R]-2,2-dimethyl-3-(2,2-dichlorovinyl) cyclopropane carboxylate m.p. 52°–3° (Compound P21/A').

EXAMPLE 16

Triphenyl phosphine (1.32 g.) was added to a well stirred solution of carbon tetrabromide (0.84 g.) in dry dichloromethane (15 ml.). t-Butyl-(±)-trans-caronaldehyde (0.5 g.) was added and the solution was stirred overnight at room temperature. After working up as described in Example 15, the crude product was distilled yielding two fractions (1) b.p. 83°–90°/0.7 mm, (0.15 g.), $n_D$ 1.4749 (2) b.p. 90°–107°/0.7 mm, (0.24 g.), $n_D$ 1.4910. The second fraction was shown (glc) to contain≈95% of the desired t-butyl-(±)-trans-[1R,3R]-2,2-dimethyl-3-(2,2dibromovinyl) cyclopropane carboxylate. (Compound P21/B').

EXAMPLE 17

The t-butyl ester described in Example 15 (280 mg.), was heated at reflux with toluene-4-sulphonic acid (55 mg.) in dry benzene (10 ml.) for 1.5 hour and cooled to give a solution of the corresponding acid. Pyridine (108.5 mg.) and thionyl chloride (126 mg.) were added and the mixture left to stand at room temperaure for 2 hours. A solution of pyridine (83.5 mg.) and 5-benzyl-3-furylmethyl alcohol (219 mg.) in dry benzene (5 ml.) was added and the mixture left to stand overnight. After chromatography or neutral alumina, the solution was evaporated to yield 296 mg. of a (±)-trans-[1R,3R] compound of formula II where $R^3$ = Cl, $R^2$ = Cl, $R^1$ = H and R = 5-benzyl-3-furylmethyl. This ester, designated ester P21A, has $n_D$ 1.5403.

The above procedure was repeated with ester P21/B' described in Example 16 to give (=)-trans-[1R,3R] ester P21/B where $R^2$ = $R^3$ = Br, R' =H, R = 5-benzyl-3-furylmethyl, $n_D$ 1.5462.

EXAMPLE 18

The conversion of the acid to the acid chloride and subsequent esterification using 5-benzyl-3-furylmethyl alcohol as described in Example 17 was repeated replacing the (±)-trans acid by other isomers of the acid and, in certain experiments, using 3-phenoxybenzyl or 3-benzylbenzyl alcohol or (±)-allethrolone or (±)-pyrethrolone or 5-propargyl-2-furylmethyl alcohol or 2,3,4,5-tetrahydrophthalimidomethyl alcohol as the alcohol to give the following esters of formula II.

| Compound | $R^3$ | $R^2$ | $R^1$ | Configuration | m.p.° | $n_D$ |
|---|---|---|---|---|---|---|
| P21C | Cl | Cl | H | (±)-trans | 61 | 1.5518 |
| P21D | Cl | Cl | H | (±)-cis | 43 | 1.5484 |
| P21E | Cl | Cl | H | (±)-cis-trans | 48.58 | 1.5445 |
| P21F | Cl | Cl | H | (±)-trans | | 1.5607 |
| P21G | Cl | Cl | H | (±)-cis | | 1.5654 |
| P21H | Cl | Cl | H | (±)-cis-trans | | 1.5694 |
| P21I | Cl | Cl | H | (±)-trans | | 1.5633 |
| P21J | Cl | Cl | H | (±)-cis | | 1.5654 |
| P21K | Cl | Cl | H | (±)-cis-trans | | 1.5701 |
| P21L | Cl | Cl | H | (±)-trans | | 1.5136 |
| P21M | Cl | Cl | H | (±)-trans | | 1.5324 |
| P21Q | Cl | Cl | H | (±)-trans | | 1.5237($n_D^{23}$) |
| P21S | Cl | Cl | H | (±)-trans | | 1.5333($n_D^{23}$) |

In compounds C, D and E, R = 5-benzyl-3-furylmethyl, in compounds F, G and H, R is 3-phenoxybenzyl, in compounds I, J and K, R is 3-benzylbenzyl, in compound L, R is (±) -allethronyl, in M, R is (±)-pyrethronyl in Q, R is 5-propargyl-2-furylmethyl and in S, R is 2.3,4,5-tetrahydrophthalimidomethyl."

The starting acid was prepared by a variant on the conventional chrysanthemic acid synthesis using ethyldiazoacetae in which, in this case, 1,1-dichloro-4-methyl-1,3-pentadiene was reacted with ethyldiazoacetate in the presence of the copper catalyst and the resulting ethyl (±)-cis-trans2,2-dimethyl-3-(2,2-dichlorovinyl)-cyclopropane carboxylate hydrolysed to the free acid. The cis- and trans-isomers can be separated from one another by selective crystallisation from n-hexane in which the cis isomer is more soluble. The isomer mixture was dissolved in hexane at room temperature and cooled to 0° or −20° C., when the trans-isomer precipitates. This precipitate was ground up, washed with a small volume of hexane at room temperature and the residue recrystallised again from hexane at 0° or −20° C., to give the trans-isomer as a residue. The cis-isomer is recovered from the hexane solution.

EXAMPLE 19 a. 5-Benzyl-3-furylaldehyde

Chromium trioxide (3.00 g.) was added to a stirred solution of pyridine (4.75 g.) in dry methylene chloride (75 ml.), and stirring was continued for 15 minutes. 5-Benzyl-3-furylmethyl alcohol (0.94 g.) was added and the mixture stirred for 15 minutes. The mixture was filtered and the residue washed with ether (100 ml). The filtrate and washings were combined and washed with 5% sodium hydroxide solution (3 × 50 ml.), 2.5N hydrochloric acid (50 ml.) and 5% sodium carbonate solution (50 ml.) and dried ($Na_2SO_4$). Yield = (0.53 g.), b.p. 116°/0.8 mm.Hg, $n_D$ = 1.5652.

b. (±)-α-Cyano-5-benzyl-3-furylmethyl alcohol

The aldehyde (1) (0.53 g.) was added to a solution of potassium cyanide (0.3 g.) in water (3 ml.) and dioxan (5 ml.) was added to effect solution. The solution was stirred for 10 minutes at 15° C., when 40% sulphuric acid (1 ml.) was added dropwise, stirring being continued for a further 10 minutes. The mixture was extracted with carbontetrachloride (50 ml.) and dried ($Na_2SO_4$). Evaporation yielded the product (0.53 g.), $n_D$ 1.5377. (The structure was confirmed by NMR).

c. (±)-α-Cynao-5-benzyl-3-furylmethyl-(±)-cis-trans3-(2',2'-dichlorovinyl)-2,2-dimethylcyclopropane carboxylate (Compound P21/N)

A mixture of the alcohol (265 mg.) prepared as described above, and 80 mg, pyridine in 10 ml. dry benzene was added to 227 mg. of (±)-cis-trans-3-(2,2-dichlorovinyl)-2,2-dimethyl cyclopropane carbonylic acid chloride in 10 ml. dry benzene. The resulting mixture was left overnight and then column chromatographed on neutral alumina. Evaporation of solvent gave 0.31 g. of Compound P21/N, $n_D$ 1.5428. (Structure confirmed by NMR).

EXAMPLE 20 a. 3-Phenoxybenzaldehyde

Chromium trioxide (3.00 g.) was added to a stirred solution of pyridine (4.75 g.) in dry methalene chloride (75 ml.), and stirring was continued for a further 15 minutes. 3-Phenoxybenzyl alcohol (1 g.) in methylene chloride (5 ml.) was added, the mixture stirred for a further 15 minutes, decanted and the residue washed with diethyl ether (100 ml.). The filtrate was washed with 55 sodium hydroxide solution (3 × 50 ml), 2.5 NHCl (50 ml.) and 5% sodium carbonate solution (50 ml.) and dried over $Na_2SO_4$ to give 3-phenoxy-benzaldehyde. Alternatively the alcohol can be oxidized using Jones' reagent, a similar yield of aldehyde being obtained. Yield (0.80 g.), b.p. 126°/0.8 mm.Hg, $n_D$ = 1.5984.

b. (±)-(α-Cyano)-3-phenoxybenzyl alcohol

3-Phenoxybenzaldehyde (0.8 g.) was added to a solutoon of potassium cyanide (0.3 g.) in water (1 ml.) at 15°. Slowly during 10 minutes 40% sulphuric acid (1 ml.) was added dropwise, stirring being continued for a further 15 minutes. The mixture was extracted with carbontotrachloride (40 ml.), dried ($Na_2SO_4$) and evaporated to yield 0.64 g. of (±)-α-cyano-(3-phenoxy)-benzylalcohol. $n_D$ −1.5832 (Structure confirmed by NMR). c) This α-cyano alcohol described above (247 mg.), pyridine (79 mg.) and (±)-cis/trans-2,2-dimethyl-3-(2,2dichlorovinyl)cyclopropane carboxylic acid chloride (227 mg.) were reacted at 20° C., in benzene (20 ml.) solution for 18 hours, which after chromatography on neutral alumina and evaporation of the solvent yielded (±)-α-cyano-3-phenoxybenzyl-(±-cis-trans-3-(2,2-dichlorovinyl)-2,2-dimethyl cyclopropane carboxylate (Compound P21/P) 260 mg.), $n_D$ 1.5561. (Structure confirmed by NMR).

EXAMPLE 21 a. 3-Benzylbenzaldehyde

Benzylbenzyl alcohol (1 g.) was oxidised using the chromium trioxide/pyridine complex as described in Example 20 a) yielding the aldehyde (0.67 g.), b.p. 124° C./0.2 mm, $n_D 20 = 1,6010$.

b. (±)-(α-Cyano)-3-benzylbenzyl alcohol

The prepared aldehyde (0.67 g.) underwent the reactions described in Example 20 b) to form the required cyanohydrin (0.41 g.), $n_D 20 = 1,5703$.

(±)-(α-Cyano)-3-benzylbenzyl-(±)-cis/trans-(2,2-dichlorovinyl)-2,2-dimethylcyclopropane carboxylate (Compound P21/Q) of $n_D 1.5462$ was prepared from the alcohol of b) above and the acid chloride following the procedure o of 20 c).

EXAMPLE 22 a. 3'-Phenoxybenzyl-3-formyl-2,2-dimethylcyclopropane carboxylate

3-Phenoxybenzyl-(+)-trans-chrysanthemate (2.0 g.) in methanol (500 g.) at −70° C., was subjected to a stream of ozone for 30 minutes. Nitrogen was passed through the solution and dimethyl sulphide (1.5 g.) added. It was allowed to warm to room temperature and stirred overnight. The solvent was evaporated and acetone (30 ml.) and 30% acetic acid (20 ml.) were added, the solution being allowed to stand for 30 minutes at 80° C. It was poured onto water (200 ml.) and extracted with ether (200 ml.). After washing with sodium carbonate solution the organic solution was dried ($Na_2SO_4$) and evaporated to give the title aldehyde. Yield (1.69 g.) $n_D 20 = 1.5558$. b. The procedure described in Example 15 was repeated using 3'-phenoxybenzyl-3-formyl-2,2-dimethyl cyclopropane carboxylate in place of t.-butyl caronaldehyde to give compound P21F (see Example 18) directly.

EXAMPLE 23

Triphenyl phosphine (13 g.) was dissolved in dry benzene (60 ml.) and methyl bromoacetate (8.3 g.) was added dropwise. The solution was heated at 70° C., for 2 days, and then cooled and filtered. The residue was washed with benzene and dried to give about 16 g. of (methoxycarbonyl methyl)triphenylphosphonium bromide. The phosphonium salt (10 g.) was dissolved in water (250 ml.) and 5% aqueous sodium hydroxide was added dropwise with stirring until the solution became alkaline to litmus. The resulting precipitate was filtered off, washed with water and dried. Crystallisation from ethyl acetate/petroleum spirit gave (methoxycarbonyl methylene) triphenyl phosphorane as a colourless solid in about 80% yield.

(Methoxycarbonylmethyl)triphenylphosphorane (3.34 g.) in methylene chloride (70 ml.) was cooled to −70° C., triethylamine (1.01 g.) was added with stirring followed by chlorine (0.77 g.) in $CCl_4$ (11 mls). Stirring was continued for 30 minutes at this temperature and for 1 hour while the reaction mixture warmed to room temperature. The reaction mixture was washed with water (3 × 50 ml.), dried over $Na_2SO_4$ and evaporated to yield 2.8 g. of chlorinated phosphorane/$Ph_3P=C(Cl)COOMe$.

A mixture of t.-butyl-trans-caronaldehyde (from ozonolysis of t.-butyl ester of (+)-trans-chrysanthemic acid) (0.7 g.) and the chlorinated phosphorane (1.3 g.) in 10 ml. dry benzene was refluxed for one hour. After distillation of the benzene, the resulting product was distilled under reduced pressure to give t.-butyl-2,2-dimethyl-3-(2-chloro-2-carbomethoxyvinyl)-cyclopropyl carboxylate, b.p. 110° C./0.4 mm, $n_D^{20}$ 1.4749 (Yield, 0.65 g.).

This compound was designated Compound P24A'.

EXAMPLE 24

The procedure described in Example 23 was repeated replacing the methyl bromoacetate by ethylbromoacetate or propylbromoacetate and by replacing the methylbromoacetate by ethylbromoacetate and replacing chlorine by bromine in the halogenation of the phosphorane step. The following compounds of formula II were obtained.

| Compound | R | $R_2$ | $R_3$ | b.p. | $n_D^{20}$ |
|---|---|---|---|---|---|
| P24B' | t.-butyl | $COOC_2H_5$ | Cl | 110–112° C/0.4mm | 1.4883 |
| P24C' | t.-butyl | $COOn-C_3H_7$ | Cl | 160–180° C/0.8mm | 1.4688 |
| P24D' | t.-butyl | $COOC_2H_5$ | Br | 120–124° C/0.04mm | 1.4830 |

EXAMPLE 25

A mixture of compound P24A' of Example 23 (320 mg.) and toluene-4-sulphonic acid (50 mg.) in dry benzene (10 ml.) were refluxed for approximately 2 hours and then cooled. 2,2-Dimethyl-3-(2-chloro-2-carbomethoxyvinyl)-cyclopropane carboxylic acid was identified in the solution by NMR. Pyridine (111 mg., 114 microliters) and thionyl chloride (132 mg., 80 microliters) were added to the solution of the carboxylic acid and the mixture was left for 3 hours at room temperatures. 2,2-Dimethyl-3-(2-chloro-2-carbomethoxyvinyl)-cyclopropane carboxylic acid chloride was identified in the solution by NMR. A solution of 5-benzyl-3-furylmethyl alcohol (210 mg.) and pyridine (88 mg., 90 microliters) in dry benzene (5 ml.) was added and the mixture left overnight at room temperature. The solution was then run through a column of neutral alumina and eluted with benzene to give 200 mg. of the 5-benzyl-3-furylmethyl ester of 2,2-dimethyl-3-(2-chloro-2-carbomethoxyvinyl)-cyclopropane carboxylic acid, $n_D^{20}$ 1.5398. This compound was designated compound P24A.

EXAMPLE 26

The procedure described in Example 25 was repeated using compounds P24B', P24C' and P24D' of Example 24 and the following compounds of formula II were obtained.

| Compound | $R_2$ | $R_3$ | $n_D^{20}$ |
|---|---|---|---|
| P24B | $COOC_2H_5$ | Cl | 1.5404 |
| P24C | $COOn-C_3H_7$ | Cl | 1.5332 |
| P24D | $COOC_2H_5$ | Br | 1.5366 |

The above three compounds are compounds of formula II where R represents 5-benzyl-3-furylmethyl.

EXAMPLE 27

Methyl-[1R-cis]-caronaldehyde was obtained by ozonolysis of methyl (+)-cis-chrysanthemate. The procedure described in Example 16 was then repeated using 5.3 g. triphenylphosphine, 3.36 g. carbon tetrabromide and 60 mls. dry dichloromethane and 1.5 g. methyl-[1R-cis]-caronaldehyde. The reaction product was then refluxed 3 hours with 9 mls. acetic acid, 6 mls. concentrated HBr and 3 mls. water and then diluted with water and extracted with ether. The organic solution was extracted with dilute sodium hydroxide and this extract acidified and extracted with ether and evaporated to give a residue of [1R-cis]-2,2-dimethyl-3-(2,2-dibromovinyl)-cyclopropane carboxylic acid.

The carboxylic acid described above was converted to its acid chloride by reaction with thionylchloride in pyridine as described in Example 17 and the resulting acid chloride reacted with 3-phenoxybenzyl alcohol in dry benzene in the presence of pyridine as described in Example 17 to give 3-phenoxy-benzyl [1R-cis-]-2,2-dimethyl-3-(2,2-dibromovinyl)cyclopropane carboxylate, m.p. 93°, $n_D$ 1.5848 (Compound P29A).

The esterification described above was repeated replacing 3-phenoxybenzyl alcohol by (±)-α-cyano-3-phenoxybenzyl alcohol to give (±)-α-cyano-3-phenoxybenzyl[1R-cis-]-2,2-dimethyl-3-(2,2-dibromovinyl) cyclopropane carboxylate, $n_D$1.5732. (Compound P 29 B). Compound P29B has $[\alpha]_D^{20} = -1°$ (C = 0.4 in ethanol). N.M.R. peaks associated with the C-H group (carbon atom bearing the α-cyano substituent) $\tau = 3.65$ and 3.72 (equal areas).

0.6 grams of the racemate was dissolved in 25 ml hexane and maintained at −20° C until precipitation of crystals was complete. The crystals were then filtered off and recrystallised from hexane to give (−)-α-cyano-3-phenoxy-benzyl [1R, cis]-2,2-dimethyl-3-(2,2-dibromovinyl)cyclopropane carboxylate, in 0.25 g yield. The physical characteristics of this crystalline isomer are as follows:

m.p. 100° C $[\alpha]_D^{20}$ + 16° (C=0.4 in ethanol)

N.M.R. Peaks associated with the C-H group (carbon atom bearing the α-cyano substituent)$\tau$= 3.65 but no peak at $\tau$=3.72.

The mother liquors were combined and evaporated to dryness to give 0.32g of the non-crystalline isomer, (+)-α-cyano-3-phenoxybenzyl [1R,cis]-2,2-dimethyl-3-(2,2-dibromovinyl)cyclopropane carboxylate having the following properties:

$n_D$ 1.5749 $[\alpha]_D$20−15° (C=0.4 in ethanol)

N.M.R. Peaks associated with the C-H bond (carbon atom bearing to the α-cyano group) $\tau$=3.72 with a small peak (20% of the 3.72 peak) at $\tau$=3.65 attributable to the crystalline isomer.

EXAMPLE 28

The esterification procedures described in Example 27 were repeated replacing the [1R-cis]-dibromovinyl acid by [1R-trans]-2,2-dimethyl-3-(2,2-dibromovinyl)-cyclopropane carboxylic acid (obtained as described in Example 16), [1R-trans]-2,2-dimethyl-3-(2,2-dichlorovinyl)cyclopropane carboxylic acid (prepared as described in Example 15) and (±)-cis-trans-2,2-dimethyl-3-(2,2-dichlorovinyl) cyclopropane carboxylic acid prepared as described in Example 18. The following esters were prepared:

3-phenoxybenzyl [1R-trans]-2,2-dimethyl-3-(2,2-dibromovinyl) cyclopropane carboxylate, $n_D$ 1.5828 (Compound P29C).

(±)-α-cyano-3-phenoxybenzyl [1R-trans]-2,2-dimethyl-3-(2,2-dibromovinyl) cyclopropane carboxylate, $n_D$ 1.5664 (compound P29D).

(±)-cyano-3-phenoxybenzyl [1R-trans]-2,2-dimethyl-3-(2,2-dichlorovinyl) cyclopropane carboxylate $n_D$ 1.5498 (Compound P29E).

(±)-α-cyano-3-phenoxybenzyl (±)-cis-trans-2,2-dimethyl-3-(2,2-dichlorovinyl) cyclopropane carboxylate, $n_D$ 1.5632 (Compound P 29F).

(±)-α-cyano-3-phenoxybenzyl (±)-cis-2,2-dimethyl-3-(2,2-dichlorovinyl) cyclopropane carboxylate, (Compound P29G), $n_D$ 1.5597.

(±)-α-cyano-3-phenoxybenzyl (±)-trans-2,2-dimethyl-3-(2,2-dichlorovinyl) cyclopropane carboxylate (Compound P29H) $n_D$ 1.5551.

(±)-α-cyano-3-phenoxybenzyl [1R,cis]-2,2-dimethyl-3-(2,2-dichlorovinyl) cyclopropane carboxylate, (Compound P29J), $n_D$ 1.5622.

(±)-α-cyano-3-phenoxybenzyl [1S,cis]-2,2-dimethyl-3-(2,2-dichlorovinyl) cyclopropane carboxylate, (Compound P29K) $n_D$ 1.5520.

The required isomer of the acid for the last four mentioned esters was obtained by resolution as described in Example 32.

EXAMPLE 29

[1R,-Trans]-3-(2,2-difluorovinyl)-2,2-dimethyl cyclopropane carboxylic acid.

a. A mixture of freshly distilled, dry, dimethyl formamide (20 ml), triphenylphosphine (7.9 g), methyl [1R,-trans]-caronaldehyde (3.0 g) and the sodium salt of chlorodifluoro acetic acid (3.6 g) were heated at 90° C with stirring for 20 hours. Water (60 ml) were then added and the solution extracted with 2 × 30 ml portions of diethylether. The combined ethereal extracts were washed with water, saturated sodium carbonate solution, saturated sodium chloride solution, and then dried over sodium sulphate and the ether distilled off. Distillation of the residue gave 2.25 g of methyl[1R,-trans]-3-(2,2-difluorovinyl)-2,2-dimethyl cyclopropane carboxylate, b.p. 63° C/20 mm, $n_D$ 1.4209.

b. An alkaline solution was prepared by dissolving sodium hydroxide (200 mg) in water (1 ml) and ethanol (10 ml) was added. The methyl ester described above (0.5 g) was stirred into the alkaline solution and the mixture was refluxed for 1 hour. The solvents were removed under reduced pressure and water (30 ml) added. The solution was washed with 2 × 20 ml portions of diethylether and acidified with concentrated hydrochloric acid. The mixture was extracted with 2 × 30 ml portions of diethylether, washed with saturated sodium chloride solution, dried over sodium sulphate and the solvents evaporated to leave 410 mg of [1R,-trans-] 3-(2,2-difluorovinyl)-2,2-dimethyl cyclopropane carboxylic acid as an oil having $n_D$ 1.4400.

EXAMPLE 30

[1R,Cis]-3-(2,2-difluorovinyl)2,2-dimethyl cyclopropane carboxylic acid.

a. The procedure described in Example 29 a above was repeated using 1.5 g methyl[1R,-cis]-caronaldehyde 2.92 g triphenylphosphine, 1.2 g sodium chlorodifluoro acetate and 7 ml dimethylformamide. The residue obtained after evaporating the final diethyl ether extract was itself extracted with 3 × 40 ml portions of petroleum ether and the petroleum ether evaporated and the residue distilled to give 440 mg of methyl [1R,-cis]3-(2,2-difluorovinyl)2,2-dimethyl cyclopropane carboxylate b.p. 74°-78° C/20 mm $n_D$ 1.4288.

b. The methyl ester obtained above (380 mg) was added to a solution of sodium hydroxide (200 mg) in water (1 ml) and ethanol (10 ml). The mixture was refluxed for 1 hour with stirring and the solvents removed under reduced pressure. Water (50 ml) was then added and the solution washed with 20 ml diethylether, acidified with concentrated hydrochloric acid and extracted with diethyl ether. The ethereal extract was washed with saturated sodium chloride, dried over sodium sulphate and evaporated to give 290 mg of [1R,-cis]-3-(2,2-difluorovinyl)-2,2-dimethyl cyclopropane carboxylic acid, $n_D$ 1.4456.

EXAMPLE 31

The acids described in Examples 29 and 30 were esterified with 5-benzyl-3-furylmethyl alcohol, 3-phenoxybenzyl alcohol and (±)-α-cyano-3-phenoxybenzyl alcohol by the following procedure. A solution of the acid (110 mg) in benzene (5 ml) was treated with pyridine (50 µl) and thionyl chloride (45 µl) and left to stand for three hours at the end of which time, the acid has been converted into its acid chloride. A solution of 3-phenoxybenzyl alcohol (137 mg) or an equivalent quantity of the other alcohols and pyridine (50 µl) in benzene (5 ml) was added to the acid chloride and the mixture left to stand over night. The desired ester was recovered from the solution by passing it through a column of neutral alumina and eluting the column with benzene. The eluate was evaporated to leave the ester as an oil, the following results being obtained.

| Compound | Acid | Alcohol | $n_D$ |
|---|---|---|---|
| P31A | 1R,-trans | 5-benzyl-3-furyl | 1.5142 |
| P31B | 1R,-trans | 3-phenoxy-benzyl | 1.5293 |
| P31C | 1R,-trans | (±)-α-cyano-3-phenoxy-benzyl | 1.5330 |
| P31D | 1R,-cis | 5-benzyl-3-furyl methyl | 1.5136 |
| P31E | 1R,-cis | 3-phenoxybenzyl | 1.5349 |
| P31F | 1R,-cis | (±)-α-cyano-3-phenoxybenzyl | 1.5355 |

EXAMPLE 32

(±)-cis-trans-2,2-dimethyl-3-(2,2-dichlorovinyl) cyclopropane carboxylic acid, prepared by reacting ethyl diazoacetate with 1,1-dichloro-4-methylpenta-1,3-diene and hydrolysing the resulting ethyl ester, was separated into the (+)-cis and (+)transisomers by selective crystalisation in n-hexane, in which the cis isomer is more soluble. The substantially pure cis and trans isomers were then resolved into their individual optical isomers by the following procedure. Resolution of (+)-cis-2,2-dimethyl-3-(2,2-dichlorovinyl)-cyclopropanecarboxylic acid. The (+)-cis acid (14.6g) in benzene (250 ml), and (+)-α-methylbenzylamine (8.47 g) in benzene (30 ml) were mixed at 50°, and allowed to cool to 20° overnight. The precipitate (13.2 g, 58% required isomer) was recrystallised 3 times from benzene to give the (+)-α-methyl benzylamine salt of the [1S,-cis] acid (1.7 g) m.p. 1350, $[\alpha]_D$-17.1° (c, 1.6 in EtOH) was isolated. Repetition, using (−)-α-methylbenzylamine gave, after 3 crystallisations, the (−)-α-methyl-benzylamine salt of the [1R,-cis] acid (6.1 g) m.p. 147° $[\alpha]_D$-26.1° (c,1.9 in EtOH) and from the mother liquors the (−)-α-methylbenzylamine salt of the [1S,-cis] acid (3.8 g) m.p. 139° $[\alpha]_D$ + 14.8° (c,2.0 in EtOH).

Each of the four salts was shaken with benzene (50 ml) and 3N HCl (50 ml) and the benzene layer processed to give the resolved acids. Thus were obtained [1S,-cis]-2,2-dimethyl-3-(2,2-dichlorovinyl) cyclopropane carboxylic acid (4.6 g) m.p. 90° $[\alpha]_D$ -26.9° (c, 1.7 in CHCl₃) and [1R,-cis]-2,2-dimethyl-3-(2,2-dichlorovinyl) cyclopropane carboxylic acid (3.9 g) m.p. 90° $[\alpha]_D$ + 27.2° (c, 2.1 in CHCl₃).

Resolution of (+)-trans-2,2-dimethyl-3-(2,2-dichlorovinyl)cyclopropane carboxylic acid The (±)-trans acid (15.6 g) in benzene (180 ml and L-(+)-threo-1-p-nitro-phenyl-2-N,N-dimethylaminopropane-1,3-diol (18.0 g) in benzene (180 ml) were mixed at 50° and cooled to 20° during 2 days. The precipitate (14.2 g) was recrystallised 3 times from trichloroethylene to give the L-(+)-threo-1-p-nitrophenyl-2-N,N-dimethylaminopropane-1,3-diol salt of [1S,-trans]-2,2-dimethyl-3-(2,2-dichlorovinyl) cyclopropanecarboxylic acid (8.9 g) m.p. 129°-131° $[\alpha]_D$ + 7.4° (c, 2.1 in EtOH). Correspondingly D-(−)-threo-1-p-nitrophenyl-2-N,N-dimethylaminopropane-1,3-diol gave the salt with the [1R,-trans] acid (9.4 g) m.p. 129-131°, $[\alpha]_D$−7.3° (c,2.0 in EtOH). Decomposition of the salts with 3N HCl as described for the cis acids gave [1S,-trans]-2,2-dimethyl-3-(2,2-dichlorovinyl)cyclopropane carboxylic acid (3.8 g) m.p. 68°-73°, $[\alpha]_d$-34.6° (c, 1.9 in EtOH) and ]1R,-trans[-2,2-dimethyl-3-(2,2-dichlorovinyl) cyclopropane carboxylic acid (4.1 g) m.p. 69-73°, $[\alpha]_D$ + 33.0° (c, 2.0 in EtOH).

The [1R,-cis] and [1R,trans] acids were converted to their acid chloride and reacted with 3-phenoxybenzyl alcohol by the procedure described in Example 1 to give the 3-phenoxybenzyl ester of [1R,-cis] and of [1R,-trans-] 2,2-dimethyl-3-(2,2-dichlorovinyl)-cyclopropane carboxylic acid, compounds P29L and P-29M respectively.

The [1R,-cis]acid was also esterified with 5-benzyl--furylmethyl alcohol by the same procedure to give compound P29N, 5-benzyl-3-furylmethyl [1R,-cis-]2,2-dimethyl-3-(2,2-dichlorovinyl) cyclopropane carboxylate.

The toxicity of these new esters was tested by the procedure described in detail in our above mentioned application and the following results were obtained:

| Compounds | Relative Toxicity | |
|---|---|---|
| | Houseflies | Mustard Beetles |
| 5-benzyl-3-furylmethyl [1R-trans]-chrysanthemate (Bioresmethrin) | 1,000 | 1,000 |
| P29L | 1,600 | 1,400 |
| P29M | 740 | 2,100 |
| P29N | 2,600 | 2,200 |

The toxicity of compounds P29L and P29M relative to bioresmethrin was also determined against the American cockroach, Periplaneta americana L. with the following results.

| Compound | Relative Toxicity |
|---|---|
| Bioresmethrin | 100* |
| P29L | 2,100 |
| P29M | 800 |

*$LD_{50}$ = 2.5 μg/insect

The following formulations are given to illustrate the way in which the insecticidal compounds of the invention can be applied to insects or environments susceptible to insect attack.

Formulation 1

Oil-based liquid spray for household insects

| | |
|---|---|
| active compound | 0.015% w/v |
| 25% Pyrethrum Extract | 0.25% |
| Piperonyl butoxide | 0.5% |
| Antioxidant | 0.1% |

Odourless light oil solvent e.g. xylene to make 100 vols.

Formulation 2

Water-based liquid spray concentrate for mosquito control

| | |
|---|---|
| active compound | 0.25% w/v |
| Piperonyl butoxide | 1.0% |
| Non-ionic emulsifier | 0.25% |
| Antioxidant | 0.1% |
| Water to make | 100 vols. |

This concentrate should be diluted 1:80 v/v with water before spraying.

Formulation 3

Aerosol

| | |
|---|---|
| active compound | 0.05% w/w |
| 25% Pyrethrum Extract | 0.8% |
| Piperonyl butoxide | 1.5% |
| Odourless petroleum distillate (b.p. 200–265°) | 17.338% |
| Propellant, e.g. a mixture of equal quantities of trichloromonofluoromethane and dichlorodifluoromethane | 80.0% |
| Perfume | 0.2% |
| Antioxidant | 0.1% |

Formulation 4

Mosquito coil

| | |
|---|---|
| active compound | 0.25% w/w |
| Tabu powder (also known as pyrethrum marc) | 30.0% |
| Filler(s), e.g. wood flour, powdered leaves or nut shells | 68.75% |
| Brilliant Green | 0.5% |
| p-Nitrophenol | 0.5% |

Formulation 5

Emulsifiable concentrate

| | |
|---|---|
| active compound | 1.5% w/w |
| Non-ionic emulsifier | 25.0% |
| Xylene | 73.4% |
| Antioxidant | 0.1% |

This concentrate may then be diluted at the rate of 30 mls. to 4½ liters of water prior to use.

Formulation 6

General purpose powder for household, garden, livestock or grain storage use

| | |
|---|---|
| active compound | 0.05% w/w |
| Tropital (the synergist piperonyl-bis-2-[2'-n-butoxyethoxy]ethyl acetal) | 0.25% |
| Antioxidant, e.g. butyl hydroxy toluene or butyl hydroxy anisole | 0.03% |
| Filler | 99.67% |

The insecticidal activity of the esters of the invention was assessed against houseflies and mustard beetles using the following techniques:

Houseflies (Musca domestica)

Female flies were treated on the thorax with a one microlitre drop of insecticide dissolved in acetone. Two replicates of 15 flies were used at each dose rate and 6 dose rates were used per compound under test. After treatment, the flies were maintained at a temperature of 20° C.+ 1° and kill were assessed 24 and 48 hours after treatment. $LD_{50}$ values were calculated in micrograms of insecticide per fly and relative toxicities were calculated from the inverse ratios of the $LD_{50}$ values. (see Sawicki et al, Bulletin of the World Health Organisation, 35,893, (1966) and Sawicki et al, Entomologia and Exp. Appl. 10,253, (1967)).

Mustard Beetles (Phaedon cochleariae Fab)

Acetone solutions of the test compound were applied ventrally to adult mustard beetles using a micro drop applicator. The treated insects were maintained for 48 hours after which time kill is assessed. Two replicates of 40 to 50 mustard beetles were used at each dose level and 3 to 4 dose levels were used for each compound. Again, $LD_{50}$ values were calculated and relative toxicities were calculated for the inverse ratios of $LD_{50}$ (see Elliott et al, J. Sci. Food Agric. 20, 561, (1969)).

Relative toxicities were calculated by comparison with 5-benzyl-3-furylmethyl (+)-trans-chrysanthemate which is one of the most toxic chrysanthemate esters known to houseflies and mustard beetles, its toxicity being about 24 times that of allethrin to houseflies and 65 times that of allethrin to mustard beetles.

The following relative toxicities were obtained.

| | Relative Toxicity | |
|---|---|---|
| Compound | Houseflies | Mustard Beetles |
| 5-benzyl-3-furylmethyl (+)-trans-chrysanthemate | 1000 | 1000 |
| Pyrethin I | 12 | 1600 |
| Bioallethrin | 60 | 20 |
| A | 1700 | 2000 |
| B | 630 | 890 |
| C | 270 | 420 |
| E | 470 | 670 |
| F | 21 | — |
| G | 18 | — |
| H | <7 | 10 |
| I | <7 | <10 |
| K | 1300 | 1600 |
| Q | 60 | 69 |
| R | 30 | 300 |
| S | 120 | 170 |
| T | 240 | 300 |
| P19A | 91 | 100 |
| P19B | 67 | 320 |
| P19C | 24 | 40 |

-continued

| Compound | Relative Toxicity | |
|---|---|---|
| | Houseflies | Mustard Beetles |
| P19D | 290 | 440 |
| P19E | 290 | 500 |
| P19F | 130 | 360 |
| P19G | 300 | 500 |
| P19H | 20 | 50 |
| P21A | 2500 | 2700 |
| P21B | 1100 | 1900 |
| P21C | 1000 | 2200 |
| P21D | 1200 | 1700 |
| P21E | 700 | 1800 |
| P21F | 400 | 790 |
| P21G | 680 | 780 |
| P21H | 660 | 740 |
| P21I | 170 | 420 |
| P21J | 360 | 350 |

| Compound | $L_D50$ (mg/kg) to rats. | |
|---|---|---|
| | oral | intravenous |
| pyrethrin I | 260–420 | 2–5 |
| 5-benzyl-3-furylmethyl (+)-trans-chrysanthemate | >8000 | 340 |
| A | 800–1000 | 120 |
| P21E | 40 | 5 |
| P21C | >400 | 26–33 |

The insecticidal activity and mammalian toxicity of certain esters of (+)-trans-2,2-dimethyl-3-(2,2-dichlorovinyl)cyclopropane carboxylic acid has been tested in a further series of experiments with the following results:

| R | Insecticidal activity | | Mammalian toxicity oral acute $LD_{50}$ mg/kg | |
|---|---|---|---|---|
| | Houseflies*[1] | German Cockroaches*[2] | Rats | Mice |
| 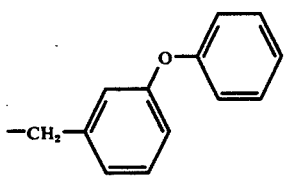 | 10.5 mg/100 ml. | 0.83 γ/insect | >300 | >300 |
| 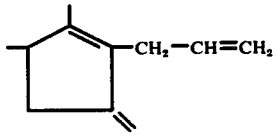 | 55 mg/100 ml. | 4.2 γ/insect | — | — |
| 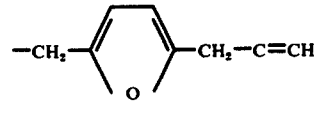 | 13 mg/100 ml. | 6.7 γ/insect | 300 | approximately 300 |
| 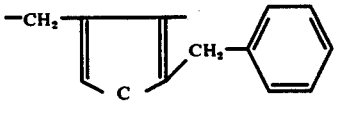 | 4.5 mg/100 ml. | 0.54 γ/insect | | 100 |
| Pyrethrin: 200–300 mg/100 ml. | 5-benzyl-3-furyl-methyl (+)-cis-trans-chrysanthemate. 0.62 γ/insect Pyrethrin: 0.8–1.4 γ/insect | | Pyrethrin 130 | |

*[1]turn table method
*[2]topical application method

| P21K | 340 | 350 |
|---|---|---|
| P21L | 72 | 73 |
| P21M | 19 | 370 |
| P21N | 100 | 2000 |
| P21P | 1300 at least | 5000 |
| P24A | 82 | 310 |
| P24B | 150 | 310 |
| P24C | 53 | 120 |
| P24D | 450 | 290 |
| P29A | 2200 | 1600 |
| P29B | 10000 | 11000 |
| P29B (crystalline isomer) | 23000 | 14000 |
| P29B (non-crystalline isomer) | 3500 | 4000 |
| P29C | 1100 | 4000 |
| P29D | 4100 | 5200 |
| P29F | 1700 | |

Mammalian toxicity of certain esters of the invention has been determined in rats with the following results:

The synergisability of certain esters of the invention has been determined in tests in which the $LD_{50}$ of the insecticide in μg. per female fly was determined by the above described methods in untreated flies and in flies pretreated with 2 μg. per fly of the synergist sesamex (2-(3,4-methylene dioxyphenoxy)-3,6,9-trioxa undecane). The following results were obtained.

| Active compound | $LD_{50}$ | | Approx. Synergistic factor |
|---|---|---|---|
| | active compound only | active compound + synergist | |
| 5-benzyl-3-furyl methyl (+)-trans-chrysanthemate 5-benzyl 3 furyl | 0.0054 | 0.00057 | 9.4 |

-continued

| Active compound | LD₅₀ active compound only | active compound + synergist | Approx. Synergistic factor |
|---|---|---|---|
| methyl (+)-cis-trans-chrysanthemate | 0.010 | 0.00079 | 13 |
| P21C | 0.0065 | 0.00033 | 19 |
| P21D | 0.0058 | 0.00046 | 12 |
| P21F | 0.013 | 0.00033 | 39 |
| P21G | 0.0083 | 0.00037 | 22 |
| A[(+)-trans-(3-cis-but-1-enyl)-isomer] | 0.0042 | 0.00033 | 13 |
| A[(+)-cis-(3-cis-but-1-enyl)-isomer] | 0.0074 | 0.0012 | 6 |

We claim:

1. A compound of the formula:

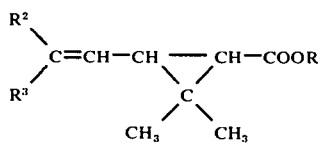

wherein:
$R^2$ and $R^3$ independently represent halogen, and R is 5-benzyl-3-furylmethyl.

2. A compound according to claim 1 which is a 5-benzyl-3-furylmethyl ester of [1R-cis]- or [1R-trans]-2,2-dimethyl-3-(2,2-dichlorovinyl) cyclopropane carboxylic acid or a mixture of the cis and trans isomers.

3. A compound according to claim 1 which is a 5-benzyl-3-furylmethyl ester of [1R,cis] or [1R,trans]2,2-dimethyl-3-(2,2-difluorovinyl) cyclopropane carboxylate.

4. A compound according to claim 1 wherein $R^2$ and $R^3$ each independently represent bromine or chlorine or fluorine.

5. A compound according to claim 1 in the form of a (+)-trans, (+-cis, (±)-trans, (±)-cis, (+)-cis-trans, or (±)-cis-trans isomer, the stereochemistry being in relation to the cyclopropane ring.

6. An insecticidal composition comprising a compound according to claim 1 together with a diluent or carrier 7. A method of insect control which comprises applying to an insect or an environment susceptible to insect attack a compound in accordance with claim 1.

8. A compound of the formula:

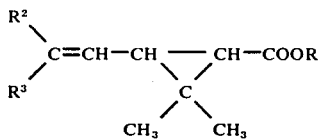

wherein:
$R^2$ and $R^3$ independently represent halogen, and R is 3-phenoxybenzyl.

9. A compound according to claim 8 which is 3-phenoxybenzyl(±)-cis-trans or (±)-cis or (±)-trans-2,2-dimethyl-3-(2,2-dichlorovinyl) cyclopropane carboxylate.

10. A compound according to claim 8 which is a 3-phenoxybenzyl ester of [1R-cis]- or [1R-trans]-2,2-dimethyl-3-(2,2-dichlorovinyl)cyclopropane carboxylic acid or a mixture of the cis and trans isomers.

11. A compound according to claim 8 which is a 3-phenoxybenzyl, ester of [1R,cis] or [1R,trans] 2,2-dimethyl-3-(2,2-difluorovinyl) cyclopropane carboxylate.

12. A compound according to claim 8 wherein $R^2$ and $R^3$ each represent bromine or each represent chlorine and R represents 3-phenoxybenzyl.

13. A compound according to claim 8 wherein $R^2$ and $R^3$ each independently represent bromine or chlorine or fluorine.

14. A compound according to claim 8 in the form of a (+)-trans, (+)-cis, (±)-trans, (±)-cis, (+)-cis-trans, or (±)-cis-trans isomer, the stereochemistry being in relation to the cyclopropane ring.

15. A compound according to claim 8, which is 3-phenoxybenzyl (±)-cis-trans-2,2-dimethyl-3-(2,2-dichlorovinyl) cyclopropane carboxylate.

16. An insecticidal composition comprising a compound according to claim 8 together with a diluent or carrier.

17. A method of insect control which comprises applying to an insect or an environment susceptible to insect attack a compound in accordance with claim 8.

18. A compound of the formula:

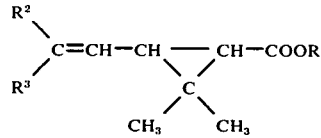

wherein:
$R^2$ and $R^3$ independently represent halogen, and R is α-cyano-3-phenoxybenzyl.

19. A compound according to claim 18 which is (±)-α-cyano-3-phenoxybenzyl [1R-trans] or [1R,cis] 2,2-dimethyl-3-(2,2-dimethyl-3-(2,2-dibromovinyl) cyclopropane carboxylate.

20. A compound according to claim 18 which is the isomer of α-cyano-3-phenoxybenzyl [1R,cis] 2,2-dimethyl-3-(2,2-dibromovinyl)-cyclopropane carboxylate having a positive $[\alpha]_D^{20}$ value when dissolved in ethanol.

21. A compound according to claim 18 which is a α-cyano-3-phenoxybenzyl ester of [1R,cis] or [1R,trans] 2,2-dimethyl-3-(2,2-difluorovinyl) cyclopropane carboxylate.

22. A compound according to claim 18 wherein $R^2$ and $R^3$ each represent bromine or each represent chlorine and R represents α-cyano-3-phenoxybenzyl.

23. A compound according to claim 18 wherein $R^2$ and $R^3$ each independently represent bromine or chlorine or fluorine.

24. A compound according to claim 18 in the form of a (+)-trans, (+)-cis, (±)-trans, (±)-cis, (+)-cis-trans, or (±)-cis-trans isomer, the stereochemistry being in relation to the cyclopropane ring.

25. A compound according to claim 18, which is (±)-α-cyano-3-phenoxybenzyl-(±)-cis-trans-2,2-dimethyl-3-(2,2-dichlorovinyl) cyclopropane carboxylate.

26. A compound according to claim 18, which is (±)-α-cyano-3-phenoxybenzyl-(±)-cis-2,2-dimethyl-3-(2,2-dichlorovinyl) cyclopropane carboxylate.

27. A compound according to claim 18, which is (±)-α-cyano-3-phenoxybenzyl[1R,cis]2,2-dimethyl-3-(2,2-dichlorovinyl) cyclopropane carboxylate.

28. An insecticidal composition comprising a compound according to claim 18 together with a diluent or carrier.

29. A method of insect control which comprises applying to an insect or an environment susceptible to insect attack a compound in accordance with claim 18.

30. A compound of the formula:

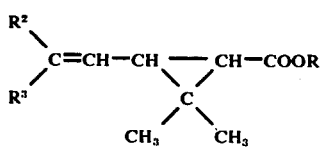

wherein:
$R^2$ and $R^3$ independently represent halogen, and R is α-cyano-5-benzyl-3-furylmethyl.

31. A compound according to claim 30 wherein $R^2$ and $R^3$ each independently represent bromine or chlorine or fluorine.

32. A compound according to claim 30 in the form of a (+)-trans, (+)-cis, (±)-trans, (±)-cis, (+)-cis-trans, or(±)-cis-trans isomer, the stereochemistry being in relation to the cyclopropane ring.

33. An insecticidal composition comprising a compound according to claim 30 together with a diluent or carrier.

34. A method of insect control which comprises applying to an insect or an environment susceptible to insect attack a compound in accordance with claim 30.

* * * * *

UNITED STATES PATENT OFFICE
CERTIFICATE OF CORRECTION

Patent No. 4,024,163           Dated May 17, 1977

Inventor(s) Michael Elliott, et al

It is certified that error appears in the above-identified patent and that said Letters Patent are hereby corrected as shown below:

[30]     Foreign Application Priority Data

August 15, 1973    United Kingdom ......... 39539/73
     October 22, 1973    United Kingdom ......... 49098/73
     June 13, 1974    United Kingdom ......... 26316/74

OTHER PUBLICATIONS

"Forkas, et al., Chem. Listy 52 688 (1958)", should read --Farkas, et al. Chem. Listy $\underline{52}$, 688 (1958)--

Column 12, lines 19 & 20: "D represents CN or C CH", should read --D represents CN or C $\equiv$ CH--

Claim 5, line 2, "(+-cis" should read --(+)-cis--

Signed and Sealed this

Sixth Day of December 1977

[SEAL]

Attest:

RUTH C. MASON          LUTRELLE F. PARKER
*Attesting Officer*       *Acting Commissioner of Patents and Trademarks*

UNITED STATES PATENT OFFICE
CERTIFICATE OF CORRECTION

Patent No. 4,024,163                     Dated May 17, 1977

Inventor(s) Michael ELLIOTT, Norman Frank JANES, and David Allen PULMAN

It is certified that error appears in the above-identified patent and that said Letters Patent are hereby corrected as shown below:

In the disclosure at:

Column 1, lines 50-55;   Correct general formula II to read

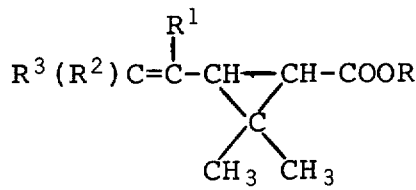

Column 4, line 67;       Change "repersents" to "represents"

Column 6, line 5;        Change "whre" to "where"

Column 11, line 62;      Change "provided does" to "provided R does"

Column 11, line 66;      Change "ozonlysed" to "ozonolysed"

Column 12, line 33;      Change "A Grignard" to "a Grignard"

Column 13, line 38;      Change "form ozonolysis" to "from ozonolysis"

Column 14, line 23;      Change "ethyl (+)" to "(±)"

Column 15, line 3;       Change "carbonaldehyde" to "caronaldehyde"

UNITED STATES PATENT OFFICE
CERTIFICATE OF CORRECTION

Patent No. 4,024,163          Dated May 17, 1977

Inventor(s) Michael ELLIOTT, Norman Frank JANES, and David Allen PULMAN

It is certified that error appears in the above-identified patent and that said Letters Patent are hereby corrected as shown below:

| | | |
|---|---|---|
| Column 16, | line 13; | Change "(±) pyethrolone" to "(+)-pyethrolone" |
| Column 17, | line 11; | Change "propyl ether" to "propyl ester" |
| Column 18, | line 46; | Change "(±)-trans[1R,3R]" to "[1R,trans]" |
| Column 18, | line 53; | Change "t-Butyl-(±)-" to "t-Butyl-(+)-" |
| Column 18, | lines 60-61; | Change "(±)-trans-[1R,3R]" to "[1R,trans]" |
| Column 19, | lines 7-8; | Change "(±)-trans-[1R,3R]" to "[1R,trans]" |
| Column 19, | line 12; | Change "(=)-trans-[1R,3R]" to "[1R,trans]" |
| Column 19, | line 20; | Change "(±)-trans acid" to "(+)-trans acid" |
| Column 19, | line 22; | Change "(±)-pyethrolone" to ""(+)-pyethrolone" |
| Column 19, | line 42; | Change "(±)-pyrethronyl" to ""(+)-pyrethronyl" |
| Column 20, | line 38; | Change "methalene" to "methylene" |

UNITED STATES PATENT OFFICE
CERTIFICATE OF CORRECTION

Patent No. 4,024,163　　　　　　　　　　Dated May 17, 1977

Inventor(s) Michael ELLIOTT, Norman Frank Janes, and David Allen PULMAN

It is certified that error appears in the above-identified patent and that said Letters Patent are hereby corrected as shown below:

| | | |
|---|---|---|
| Column 25, | line 56; | Change "(+)-cis and (+)transisomers" to "(±)-cis and (±)-trans isomers" |
| Column 25, | line 61; | Change "(+)-cis-" to "(±)-cis-" |
| Column 25, | line 62; | Change "(+)-cis" to "(±)-cis" |
| Column 26, | line 17; | Change "(+)-trans-" to "(±)-trans-" |
| Column 30, | line 13; | Change "(+)-trans-" to "(±)-trans-" |
| Column 30, line 46; (fifth entry under "German Cockroaches"); | | Change "5-benzyl-3-furylmethyl (+)" to "5-benzyl-3-furylmethyl (±)" |
| Column 31, line 7; (first entry under "Active compound"); | | Change "methyl (+)-cis-" to "methyl (±)-cis-" |

In the Claims:

| | | |
|---|---|---|
| Claim 11, | line 3; | "dimethyl-3-(2,2-difluorovinyl cyclopropane" should read --dimethyl-3-(2,2-difluorovinyl) cyclopropane-- |

UNITED STATES PATENT OFFICE
CERTIFICATE OF CORRECTION

Patent No. 4,024,163                    Dated May 17, 1977

Inventor(s) Michael ELLIOTT, Norman Frank JANES, and David Allen PULMAN

It is certified that error appears in the above-identified patent and that said Letters Patent are hereby corrected as shown below:

Claim 19, line 3;   "2,2-dimethyl-3-(2,2-dimethyl-3-(2,2-dibromovinyl)"
should read
--2,2-dimethyl-3-(2,2-dibromovinyl)--

Signed and Sealed this
Twenty-third Day of May 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,024,163
DATED : May 17, 1977
INVENTOR(S) : MICHAEL ELLIOTT et al

It is certified that error appears in the above—identified patent and that said Letters Patent is hereby corrected as shown below:

Column 1, line 62, after "when" insert --$R^2$ represents methyl, or--.

Signed and Sealed this

Twelfth Day of April 1983

[SEAL]

Attest:

Attesting Officer

GERALD J. MOSSINGHOFF

Commissioner of Patents and Trademarks

UNITED STATES PATENT AND TRADEMARK OFFICE

CERTIFICATE EXTENDING PATENT TERM
UNDER 35 U.S.C. 156

Patent No.    : 4,024,163

Dated         : May 17, 1977

Inventor(s)   : Michael Elliott, et al

Patent Owner  : National Research Development Corporation

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this Eleventh day of March 1987.

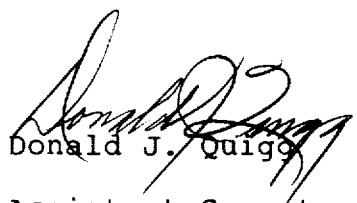

Donald J. Quigg

Assistant Secretary and Commissioner of Patents and Trademarks